(12) United States Patent
Driscoll et al.

(10) Patent No.: US 9,714,893 B2
(45) Date of Patent: Jul. 25, 2017

(54) PARTICLE SIZE DISTRIBUTION PROFILES AND USE THEREOF TO ADJUST A DISPERSION CHARACTERISTIC

(75) Inventors: David F. Driscoll, Bridgewater, MA (US); David F. Nicoli, Goleta, CA (US)

(73) Assignee: STABLE SOLUTIONS LLC, Goleta, CA (US)

( * ) Notice: Subject to any disclaimer, the term of this patent is extended or adjusted under 35 U.S.C. 154(b) by 789 days.

(21) Appl. No.: 13/509,398

(22) PCT Filed: Nov. 10, 2010

(86) PCT No.: PCT/US2010/002940
§ 371 (c)(1),
(2), (4) Date: Aug. 1, 2012

(87) PCT Pub. No.: WO2011/059485
PCT Pub. Date: May 19, 2011

(65) Prior Publication Data
US 2012/0318051 A1    Dec. 20, 2012

Related U.S. Application Data

(60) Provisional application No. 61/272,879, filed on Nov. 13, 2009.

(51) Int. Cl.
*G01N 15/02*    (2006.01)
(52) U.S. Cl.
CPC .................... *G01N 15/02* (2013.01)
(58) Field of Classification Search
CPC ............... G01N 15/0612; G01N 15/06; G01N 15/1056; G01N 2015/1087; G01N 15/02; G01N 15/0205

(Continued)

(56) References Cited

U.S. PATENT DOCUMENTS 5,094,532 A    3/1992   Trainer et al.
5,835,211 A    11/1998  Wells et al.
(Continued)

OTHER PUBLICATIONS

Newton, D.W., "The Role of Temperature in the Life of a Pharmaceutical Preparation", Pharmacopeial Forum, vol. 25, No. 1, pp. 7655-7661 (Jan.-Feb. 1999).

(Continued)

*Primary Examiner* — Daniel S Larkin
*Assistant Examiner* — Anthony W Megna Fuentes
(74) *Attorney, Agent, or Firm* — Buchanan Ingersoll & Rooney PC

(57) ABSTRACT

A method for identifying an improved particle size distribution profile of a dispersion, the method including: (a) providing a dispersion comprising a liquid and particles dispersed in the liquid; (b) measuring a particle size distribution of the dispersion, resulting in a first particle size distribution profile; (c) adjusting at least one parameter associated with the dispersion; (d) measuring a dispersion characteristic, after adjustment of the at least one parameter; and (e) measuring the particle size distribution of the dispersion after adjustment of the at least one parameter, resulting in a second particle size distribution profile; wherein each of the first and second particle size distribution profiles comprises a plurality of data points of particle concentration values as a function of particle size.

28 Claims, 6 Drawing Sheets

(58) Field of Classification Search
USPC .......... 73/61.71, 61.48, 865.5; 356/335, 356
See application file for complete search history.

(56) References Cited

U.S. PATENT DOCUMENTS

| | | | |
|---|---|---|---|
| 6,109,098 | A | 8/2000 | Dukhin et al. |
| 6,119,510 | A | 9/2000 | Carasso et al. |
| 6,473,177 | B2* | 10/2002 | Yamaguchi .................. 356/336 |
| 6,794,671 | B2 | 9/2004 | Nicoli et al. |
| 7,010,979 | B2 | 3/2006 | Scott |
| 7,127,356 | B2 | 10/2006 | Nicoli et al. |
| 7,150,996 | B2* | 12/2006 | Nicoli et al. .................. 436/69 |
| 7,331,233 | B2 | 2/2008 | Scott |
| 7,610,822 | B2 | 11/2009 | Volker |
| 2002/0058654 | A1* | 5/2002 | Coats .................. C07C 237/22 514/217.03 |
| 2002/0096111 | A1* | 7/2002 | Shutic et al. ................. 118/308 |
| 2004/0060356 | A1 | 4/2004 | Scott |
| 2005/0262927 | A1 | 12/2005 | Scott |
| 2007/0091301 | A1 | 4/2007 | Volker |
| 2007/0110777 | A1* | 5/2007 | Joabsson et al. ............. 424/401 |

OTHER PUBLICATIONS

Guyton, A.C., "The Microcirculation and the Lymphatic System: Capillary Fluid Exchange, Interstitial Fluid, and Lymph Flow", Textbook of Medical Physiology, Eighth Edition, pp. 170-171 (1999).

"Lipid Injectable Emulsion", USP/NF, Liotrix, Official Monographs, pp. 3694-3695 (2009).

"Propofol", USP/NF, Propofol, Official Monographs, pp. 4447-4450 (2009).

"FDA Safety Alert: Hazards of Precipitation Associated With Parenteral Nutrition", Department of Health & Humans Services (Apr. 18, 1994).

"Particulate Matter in Injections", Physical Tests, USP 788, pp. 339-343 (2009).

"Particulate Contamination: Sub-Visible Particles", European Pharmacopeia 8th Edition Council of Europe, Strasbourg, Chapter 2.9.19., pp. 253-255 (2005).

"Globule Size Distribution in Lipid Injectable Emulsions", Eltrophoresis, Physical Tests, USP 729, pp. 310-312 (2012).

Nath, N. et al., "Particulate Contaminants of Intravenous Medication and the Limits Set by USP General Chapter <788>" (2004).

Granum, B. et al., "Forum—The Effect of Particles on Allergic Immune Responses", Toxicological Sciences, vol. 65, pp. 7-17 (2002).

Driscoll, K.E. et al., "Cytokines and Particle-Induced Inflammatory Cell Recruitment", vol. 105, Supplement 5, Environmental Health Perspectives, pp. 1159-1164 (Sep. 1997).

Nygaard, U.C. et al., "The Allergy Adjuvant Effect of Particles—Genetic Factors Influence Antibody and Cytokine Responses", BMC Immunology, vol. 6, No. 11, pp. 1-10 (Jun. 21, 2005).

Giezen, T.J. et al., "Safety-Related Regulatory Actions for Biologicals Approved in the United States and the European Union", JAMA, vol. 300, No. 16, pp. 1887-1896 (Oct. 22/29, 2008).

Carpenter, J.F. et al., "Commentaries—Overlooking Subvisible Particles in Therapeutic Protein Products: Gaps That May Compromise Product Quality", Journal of Pharmaceutical Sciences, vol. 98, No. 4, pp. 1201-1205 (Apr. 2009).

International Search Report (PCT/ISA/210) issued on Aug. 2, 2011, by the Korean Intellectual Property Office as the International Searching Authority for International Application No. PCT/US2010/002940.

* cited by examiner

PARTICLE SIZE DISTRIBUTION PROFILES AND USE THEREOF TO ADJUST A DISPERSION CHARACTERISTIC

CROSS-REFERENCE TO RELATED APPLICATIONS

This application is a national stage filing under 35 U.S.C. §371 of PCT/US2010/002940 filed as an International Application on Nov. 10, 2010 designating the U.S., which claims the benefit under 35 U.S.C. §119 of U.S. Provisional Application No. 61/272,879 filed on Nov. 13, 2009. The entire contents of these applications are hereby incorporated by reference in their entireties.

BACKGROUND

Field

The present disclosure relates to the identification and use of particle size distributions (PSDs), hereinafter referred to as PSD profiles, associated with particle/globule-containing liquid suspensions, dispersions, and/or solutions. The PSD profiles can be used for optimizing liquid suspensions, dispersions or solutions with respect to their quality, efficacy (performance), and/or safety.

Related Art

Particle- or globule-containing suspensions, dispersions or liquids can be used for a wide variety of commercial processes, products and applications. Three examples, among many, include: 1) pigment-based suspensions, such as water-based paints and inks; 2) injectable dispersions used for medical purposes, such as for drug delivery; and, 3) alcoholic or non-alcoholic beverages.

SUMMARY

According to an exemplary aspect, a method for identifying an improved particle size distribution profile of a dispersion is provided, the method comprising:

(a) providing a dispersion comprising a liquid and particles dispersed in the liquid;

(b) measuring a particle size distribution of the dispersion, resulting in a first particle size distribution profile;

(c) adjusting at least one parameter associated with the dispersion;

(d) measuring a dispersion characteristic, after adjustment of the at least one parameter; and (e) measuring the particle size distribution of the dispersion after adjustment of the at least one parameter, resulting in a second particle size distribution profile;

wherein each of the first and second particle size distribution profiles comprises a plurality of data points of particle concentration values as a function of particle size.

According to an exemplary aspect, the dispersion contains particles in an amount of about 1% to about 40% w/v.

According to an exemplary aspect, the dispersion is a lipid emulsion, a liposomal preparation, a micellar suspension, a colloidal or biologic/protein-based dispersion, or a solution containing particles, and wherein the dispersion is intended for intravenous administration.

According to an exemplary aspect, each particle size distribution profile consists of data points of particles having a particle size in the range of about 0.01 to about 100 micrometers.

According to an exemplary aspect, the particle size distribution profiles are measured with a single-particle optical sensing technique.

According to an exemplary aspect, the first particle size distribution profile and the second particle size distribution profile comprise substantially the same data points.

According to an exemplary aspect, the first and second particle size distribution profiles each comprise at least 10 data points within the range of 0.01 to 100 micrometers.

According to an exemplary aspect, the further comprises determining whether a change in the dispersion characteristic can be attributed to a feature of the second particle size distribution profile, to define a tolerable limits threshold.

According to an exemplary aspect, the dispersion characteristic is selected from the group consisting of a dispersion stability, an efficacy of an active ingredient, and an occurrence and/or a severity of an adverse active ingredient-induced event.

According to an exemplary aspect, the dispersion characteristic is a degree of particle agglomeration at a predetermined time after dispersion formation.

According to an exemplary aspect, the method further comprises determining a concentration of particle agglomerations having a particle size of at least about 5 times the size of the average particle size of unaggregated primary particles, in the dispersion.

According to an exemplary aspect, the parameter associated with the dispersion is selected from the group consisting of: a material used to form the dispersion, a condition of a process for forming the dispersion, a material used to contain the dispersion, and a condition of storing and/or transporting the dispersion.

According to an exemplary aspect, the step (d) of measuring a dispersion characteristic comprises subjecting the dispersion to forced accelerated degradation conditions.

According to an exemplary aspect, the method further comprising, after step (e):

(f) adjusting at least one parameter associated with the dispersion;

(g) after step (f), measuring the dispersion characteristic; and (h) measuring the particle size distribution of the dispersion after adjustment of the at least one parameter, resulting in a third particle size distribution profile.

According to an exemplary aspect, steps (f), (g) and (h) are repeated until a predetermined condition of the dispersion characteristic is satisfied.

According to an exemplary aspect, the predetermined condition is a predetermined concentration level of agglomerated particles of at least a predetermined particle size.

According to an exemplary aspect, a method for improving a sample-to-sample consistency of a process for forming a dispersion is provided, the method comprising the method of claim 1, wherein each of steps (b), (d) and (e) are conducted for at least two samples of the dispersion, wherein the at least two samples are formed in different batches in a batch process, or at different times in a continuous or semi-continuous process.

DETAILED DESCRIPTION

Figure 1:
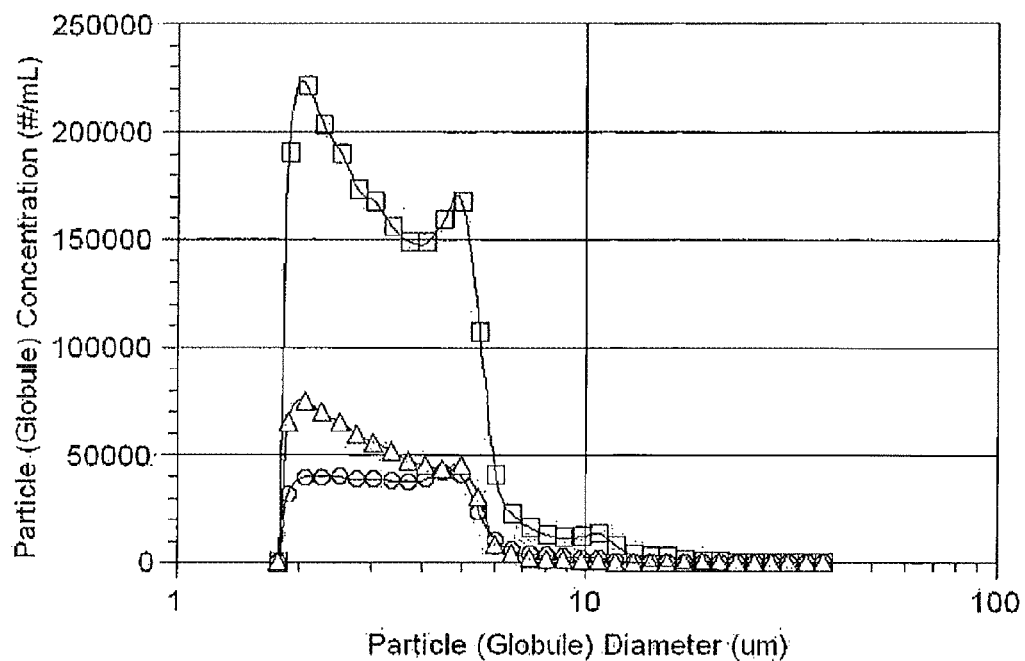
FIG. 1 is a graph showing a particle size distribution profile, globule concentration (number of globules/mL) vs. diameter (μm), obtained by SPOS for o/w emulsions (Manufacturer "A") having oil concentrations (w/v) of 10% (open circles), 20% (open triangles) and 30% (open squares), according to an exemplary aspect.

The following acronyms/abbreviations are used in the present application:
ACF: autocorrelation function
CMP: chemical mechanical planarization
CV: coefficient of variation
DLS: dynamic light scattering
FD: Fraunhofer diffraction
GSD: globule size distribution
LE: light extinction
LS: light scattering
MS: Mie scattering
OVA: ovalbumin
PCS: photon correlation spectroscopy
PHD: pulse height distribution
PM: particulate matter
PSD: particle size distribution
PSP: polystyrene particles
RES: reticuloendothelial system
SD: standard deviation
SOP: standard operating procedure
SPOS: single particle optical sensing
TLT: tolerable limits threshold
VFD: volume fraction distribution.

Multiple formulation-related factors or parameters affecting the physicochemical stability and compatibility of suspensions, dispersions, liquids and/or solutions are closely related to the detailed shape, or "profile", of the PSD. Applicants have recognized that those factors may be significantly altered by changes in the PSD, which can in turn affect the quality, efficacy (performance), and/or safety of the suspensions, dispersions, liquids and/or solutions.

A method is provided for creating and optimizing liquid formulations through identification of certain physical features or markers or landmarks in the associated particle size distribution (PSD) that forms a "signature" of the end product that is linked to its optimized performance. Using appropriate measurements and associated instrumentation for obtaining the PSD signature, a specific dispersion or solution having optimal properties can be manufactured. The resulting PSD can be intentionally designed, e.g., emulsions, within pre-defined, desirable limits, or, the resulting PSD can be unintended, e.g., particulates in solution that are randomly introduced due to process or product defects associated with manufacturing. The PSD can also be affected by chemical and/or physical changes that can occur during its packaging and/or shelf life. A desirable and unique PSD profile can be identified and controlled by the methods taught herein. Precise particle or droplet size domains can be constructed, containing upper and/or lower boundaries, thus defining the design space of the PSD signature. Subsequent pass/fail manufacturing specifications can be established using a tolerable limits threshold profile as the design space for a product in order to reproduce the desired PSD signature associated with peak performance and/or safety.

According to an exemplary aspect, a method is provided for identifying the optimal physical profile of the particle/globule size distribution, or PSD/GSD, for a given formulation or product. According to another exemplary aspect, from this optimal profile, permissible "outer boundaries" of the PSD/GSD profile that define the optimal stability, compatibility, efficacy, and possibly safety, of an end product can be established. These boundaries can form the preferred design space within the PSD and constitute the "tolerable limits thresholds", or TLT, design space. According to another exemplary aspect, from the boundaries of the PSD/GSD profile, or its TLT design space, a useful PSD/GSD "signature" can be derived. According to another exemplary aspect, the PSD/GSD signature can become the benchmark, or standard, by which all subsequent manufactured batches of a given dispersion are measured, in order to ensure their effective similarity to what has been previously established to be an ideal, optimized formulation.

The dispersion can include any liquid-based material containing particles dispersed in a liquid. As used herein, the term "particle" includes both a solid phase particle as well as a liquid phase droplet, and such terms "particle" and "droplet" are used interchangeably with respect to identifying an ideal PSD signature for a given formulation or product. The dispersion can include a suspension, an emulsion, a solution, or mixtures thereof. Solutions can be included in view of the presence therein of insoluble particles, whether intended or unintended. For example, intended particles contained in a solution may be a natural part of the product and, for example, may be able to absorb and/or scatter light within the visible color spectrum, thus determining the color of the liquid. Such solutions can be purely aqueous-based or, for example, can be mixtures of water and less polar liquids, such as alcohol. Concord grape juice is an example of an aqueous dispersion, whereas cabernet red wine is an example of a hydroalcoholic dispersion. Unintended particles in solutions can arise from a variety of sources and can be introduced, in ways both foreseen and unforeseen, for example, during the manufacturing and packaging processes associated with a given formulation and end product. Such unintended particles can also be produced as a result of various physical and chemical interactions between ingredients in a product or with its packaging container. These particles may or may not pose an obvious or significant adverse effect on a given formulation. It can be advantageous to reduce or minimize the presence of such particles. In an exemplary aspect, the solution contains particles having a particle size of greater than 50 micrometers, in an amount of less than about 1%, for example less than about 0.01%, of the total particles in the solution.

The terms "particles", "droplets", and "globules" are used interchangeably throughout the disclosure with respect to identifying an ideal PSD signature for a given formulation or product. The term "particle size distribution", or PSD, also encompasses a globule size distribution, or GSD, and a PSD profile encompasses a GSD profile. Particles in dispersions can include homogenous suspension of insoluble solids, and when they are dispersed in the surrounding liquid phase, the resulting mixture can be referred to as a suspension. When conventional suspensions become unstable, the particles can flocculate or agglomerate and can eventually settle, or sediment, to the bottom of the liquid phase (if they are large enough and dense enough relative to the surrounding liquid), in some cases forming a solid cake. Droplets in dispersions can include a homogenous suspension of one liquid component (i.e., internal phase) surrounded by a second immiscible liquid (i.e., external phase). When droplets of the first liquid are dispersed with the aid of a surfactant in the surrounding second liquid phase (e.g., water, if it is an oil-in-water mixture; oil, if it is a water-in-oil mixture), thereby forming a single, homogenous suspension, the resulting mixture can be referred to as an emulsion. When emulsions become unstable, the small liquid droplets can agglomerate at a much faster rate than in a stable emulsion. They can coalesce with one another on a relatively much faster time scale, forming in the process large globules that can eventually undergo irreversible separation of the oil and water phases. In an unstable oil-in-water emulsion, for example, if the internal oil phase is less dense than the external water phase, visibly evident separation of the oil phase can eventually manifest itself as oil floating on top of the aqueous phase, and vice-versa if the oil phase is denser than the aqueous phase. As used herein, the "particle" encompasses a particle, a droplet, and a globule.

The occurrence of other particles in a solution can reflect the natural characteristics of the product. These particles can, for example, be the unintended consequence of the manufacturing steps and/or changes in the active ingredients, leading to the formation of aggregates or microprecipitates, thus altering the solubility/homogeneity of the original product. Particles may grow in size and number (i.e., concentration) over the shelf life of the product as a function of ongoing destabilization. Certain steps can be taken to minimize their occurrence, but in some cases it may not be possible to avoid the presence of such particles in a given formulation. The particles in such formulations can be either visible or subvisible, depending on their size, and can vary in size and concentration, depending on the composition of the formulation. The particles can span a broad size range, encompassing several orders of magnitude (for example, 0.01 to 100 micrometers). In exemplary formulations, unintended particles in solutions will be invariably present to one degree or another, no matter what steps are taken to eliminate them. As such, these "solutions" can be technically characterized as "dispersions", since the insoluble particles can be suspended (albeit only temporarily in the absence of a suspending agent) by gentle agitation prior to use.

Additional terms that are used in this application to characterize the distribution of particles (intended or unintended) in various liquid-based systems are described herein. Provided is a method for identifying a suitable or ideal PSD associated with the optimal performance of a given product, referred to hereinafter as the "PSD Signature". In the course of analyzing the factors that ultimately lead to the identification of the PSD Signature of a given formulation, other terms describing sub-optimal PSDs can be encountered, and they can also be used in this application. For example, the initial particle size analysis of an unrefined product may yield a PSD having a certain "structure" or "shape" (i.e., narrow vs broad, unimodal vs multimodal distribution). If the shape, or structure, of the PSD is reproducible from batch to batch, then the formulation can possess a certain unique PSD "profile". The shape can include features such as a maximum, a minimum, a relative maximum or a relative minimum, an inflection point, etc., which can be related to a change in the dispersion characteristic. This, in effect, can be the starting point from which the formulation can be assessed, and the process can be gradually refined to establish its PSD signature.

According to an exemplary aspect, each particle size distribution profile can comprise a plurality of data points of particle concentration values as a function of particle size, for example, at least about 10 data points, for example at least about 100 data points, for example at least about 1000 data points, for example, less than about 10,000 data points. Multiple iterations of particle size distribution measurements can be conducted, each resulting in a distinct particle size distribution profile. In an exemplary embodiment, the first particle size distribution profile and the second particle size distribution profile can comprise substantially the same data points. Each particle size distribution profile can include data points of particles having a particle size in the range of about 0.01 to about 100 micrometers. Whether a change in the dispersion characteristic is attributed to a feature of a particle size distribution profile can be determined, for example, by comparing the particle size distribution profiles and dispersion characteristic measurements.

At least one parameter associated with the dispersion can be adjusted, and the effect of such adjustment upon the particle size distribution and/or dispersion characteristic can be observed and/or measured. The parameter associated with the dispersion can include, for example, a material used to form the dispersion, a condition of a process for forming the dispersion, a material used to contain the dispersion, and a condition of storing and/or transporting the dispersion.

To identify the PSD signature, the PSD profile can be linked to some characteristic of the dispersion, for example product performance of the dispersion including, for example, dispersion stability, an efficacy of an active ingredient, an occurrence and/or a severity of an adverse active ingredient-induced event such as an allergic reaction, taste, surface coating uniformity, print quality, infusion efficiency or safety, to name only a few such aspects/parameters. For example, the dispersion characteristic can include a degree of particle agglomeration at a predetermined time after dispersion formation. The concentration of particle agglomerates having an average particle size of at least about 5 times the size of the unaggregated primary particles can be measured. Once a certain PSD profile is linked to a preselected desirable outcome, the stability (resistance to change over time) of the profile can be evaluated under various stress conditions such as under forced accelerated degradation studies (see, for example, U.S. Pat. No. 7,150,996 to Nicoli et al) to determine whether the product performs as intended throughout its manufacturer-assigned shelf life. Such "stress testing" of the product can establish the ability of the PSD profile to identify its stability. There can be certain "boundaries" associated with the PSD profile that determine the performance of the product. Once the boundaries distinguishing between passing and failing products are determined, a unique product identifier can be devised. These defined boundaries can become the "tolerable limits threshold", or TLT, that can establish the "design space" or product specification, simply referred to as the "PSD signature".

The presence of an excess concentration of extraneous particles can produce an undesirable interaction with an active ingredient(s), for example, through an incompatibility and/or instability that can cause the product to fail upon application or produce bodily harm. Thus, a "tolerable" limit of these "stray", or "outlier", particles or droplets can exist for each formulation. At or below such tolerable limit, they will not produce undesirable effects, as defined by the PSD of the individual product's design space. Therefore, each product can have associated with it a unique PSD signature that is indicative of a pass/fail condition with regard to its commercial distribution and intended application. It can be desirable to know the acceptable population (for example, concentration, #/mL) of such particles or droplets falling within the PSD signature, in order to reduce or eliminate the number of products which deviate outside an established set of tolerable limits over time, for example, over the shelf life of the product, thus maintaining its effectiveness for the intended application. It can be beneficial to recognize that each product, given its unique composition, can have associated with it a unique PSD signature. For example, this signature may not necessarily conform with conventional definitions of "quality", such as indicating the difference between a "fine" and "coarse" dispersion. In an exemplary embodiment, the shape of a particular PSD signature is relevant only with respect to the performance of a given final product with which that PSD signature is associated, irrespective of its fineness or coarseness.

According to an exemplary aspect, a particular design space can be identified based on specific boundaries of the PSD that can establish the stability and efficacy, and therefore the shelf life, of the product. When the desired PSD signature is not obtained for a newly produced batch of a given product, this absence can signal an underlying defect in the manufacturing process, which can in turn initiate a comprehensive search for possible cause(s) of the deviation, for example, from the procurement of raw materials all the way through the processes involved in producing the final packaged product. This finding can lend confidence to the significance of out-of-specification PSD signatures. Therefore, a significant alteration in the PSD profile, for example, excessive particle concentration (over a given size range), and/or growth in particle size over time relative to an established design space or optimized PSD signature—can be viewed as a harbinger of a potential impending product failure. If the PSD profile is too fine (for example, much of the particle concentration is below the lower boundary limit of its PSD signature), so that it adversely affects product performance, similar measures can be taken to identify possible cause(s) of the deviation, and corrective action can be taken.

Thus, an exemplary aspect relates to novel means for developing optimized dispersions, including emulsions, suspensions, solutions and other liquid-based formulations. In one embodiment (for example, emulsions and suspensions), the population of particles or droplets is specifically designed, or intended, to be a homogenously dispersed formulation. The most desirable dispersed phase of these suspensions or emulsions can be predetermined in terms of its composition and physical stability. The dispersed phase can encompass a broad concentration range, for example, from about 1% to about 60% (w/v), or more, or from about 1% to about 40% (w/v), or from about 0.001% to about 40% (w/v). The shelf life of these products can be equally variable, with a similarly broad range of stability limits, for example, from as little as two weeks (or at least two weeks) to as long as two years (or at least two years) or more. There can be significant variability in the quality of the dispersions, and development of specific forced accelerated degradation methods, for example, involving ionic stress, temperature, humidity, oxidation, hydrolysis and photolysis, can be used to accelerate the rate of agglomeration of the suspended particles/droplets and thereby assist in identifying those formulations that are most susceptible to failure over time and upon use or application (Nicoli et al, 2006).

There are many examples of oil-in-water emulsions that are of great commercial value, such as water-based paints and bitumen, or asphalt, emulsions, to name only two examples. In these applications, product failures (for example, involving instability or incompatibility) can manifest themselves at the time of application (for example, premature chipping of paints or compromised microsurfaces of roadways), and the consequences can be costly (for example, product recalls or re-pavement of road surfaces, respectively). Another example can involve ink used in inkjet cartridges. Failure to control the PSD signature could result in a higher incidence of clogging of the orifice that releases the ink during printing, possibly prompting the disposal of entire batches of cartridges immediately after filling and prior to commercial distribution. The economic losses are greatly magnified if the inkjet cartridges reach commercial distribution and subsequently fail during use because of aggregation and coalescence of ink pigment droplets and resulting orifice clogging during use, prompting a widespread product recall.

Another practical and similarly costly example of product instability and subsequent degradation involves the suspensions, or "slurries", used in chemical mechanical planarization (CMP) of silicon wafers between the processing steps used in integrated circuit production. If the slurry PSD is not well-controlled and monitored prior to use, the surfaces of the computer chips may be scratched by over-size particles, thus reducing the yield of undamaged circuits. If not closely monitored, use of a sub-optimal CMP slurry can be very costly, as computer chip production schedules can run 24 hours per day and 7 days per week, for example, resulting potentially in lost revenue of many millions of dollars per day.

By virtue of their widespread applications, the dispersions and emulsions mentioned above can be mass-produced in very large batch quantities of, for example, 1,000 to 15,000 liters, and ideally can be designed to last a significant, predefined period of time (shelf life) until use. Efforts can be made to extend the shelf life of such products by optimizing product and manufacturing conditions through forced degradation testing. However, at the very least, there is a reasonable expectation that the manufacturing processes for established products will be cost-effective, with a high pass/fail ratio for each commercial formulation. The above examples illustrate some of the possible consequences of the use of externally applied formulations having PSD profiles that are not well-controlled and therefore sub-optimal—which can be particularly important issues for the production of high volume and/or high cost products.

Other commercial dispersions can also be adversely affected by unintended alterations in their PSD profiles, or signatures. For example, homogenized milk is an oil-in-water emulsion—a dispersion of dairy fat droplets suspended in water and ionically stabilized by an adsorbed electrically-charged protein, bovine casein, which typically has a very short shelf life, approximating two weeks under refrigeration. The stability of this dispersion is influenced by the processing steps carried out prior to commercial distribution (for example, homogenization and sterilization) and can depend upon minimizing exposure to temperatures above 40° F. for the life of the final packaged product (Newton, 1999). A failure to maintain refrigerated temperatures at any stage (pre- or post-commercial distribution) can promote its instability, which in its early stages is manifested by a sour odor and taste. In another example involving food products, fermentation of grapes for the production of red wine can ultimately lead to a hydroalcoholic dispersion of pigments supplied by the grape skins. The quality of a particular vintage is generally believed to be influenced mostly by the weather conditions in that year. Classic vintages of red wine from a particular grape harvest are highly desirable, but they occur infrequently. The role of a particular PSD during the aging of barrels of wines in cellars has not been explored on a systematic basis. Rather than using standard age periods or other subjective or qualitative measures for verifying the readiness of specific wines, it can be possible that routine sampling for quantitative confirmation of an optimum PSD signature would better identify the best time for bottling and distribution.

There are numerous other product formulations involving aqueous dispersions where product failure can have unacceptably high safety risks, specifically including injectable dispersions designed for medical use. This can especially be the case for products designed to be administered by intravenous injection, such as lipid emulsions, liposomal and micellar preparations, colloids, and biologic/protein-based solutions. The inhomogeneous separation of the dispersed phase from the continuous phase can have potentially life-threatening consequences, such as the mechanical obstruction of the microvasculature (for example, capillaries, venules and arterioles) or even larger vessels of the circulatory system. Embolization of vessels can deprive vital organs (for example, lungs, heart, liver and brain) or other highly perfused organ systems (for example, kidney, gastrointestinal tract and extremities) of oxygen and nutrients, that could induce ischemic injury, cell death, organ failure or limb amputation.

To protect the public from potentially adverse health effects arising from the use of unstable injectable emulsions, the U.S. Pharmacopeia has established droplet size limits at two size thresholds. The first limit is with respect to the mean droplet size, expressed as the light scattering intensity-weighted mean droplet diameter, not to exceed 500 nanometers. The second limit is with respect to the large-diameter "tail" of over-size fat globules, expressed as the volume-weighted percentage of total fat that resides in globules larger than five micrometers (µm), or $PFAT_5$, not to exceed 0.05% (v/v). (USP, 2009) The 5-µm threshold limit for large-diameter fat globules acknowledges the dimensions of the smallest-diameter human blood vessels, for example, capillaries, approximately 4 µm in diameter (Guyton, 1991), and the possible development of fat embolism. These globule size limits have been set irrespective of the concentration of the dispersed lipid phase of commercial injectable emulsion formulations, which typically is between 10 and 30% (w/v). Moreover, these limits apply to all injectable emulsions, whether they are intended for nutritional support purposes (Lipid Injectable Emulsions, USP/NF, 2009) or as drug delivery vehicles (Propofol Injectable Emulsion, USP/NF 2009).

In terms of human safety, the presence of potentially embolic particles, aggregates or microprecipitates in injectable drug solutions designed for intravascular administration poses a far greater risk than the existence of over-size, large-diameter fat globules in injectable emulsions, owing to the physical differences between them. For example, fat globules in intravenous emulsions are derived from natural oil substances (e.g., plant-derived medium- and long-chain triglycerides) and are mechanically flexible. Therefore, their metabolic fate in the bloodstream is very different from that of rigid particles found in intravenous solutions (e.g., glass or metal particles, dirt, cotton fibers and crystalline precipitates), arising from various natural or unnatural sources or conditions. Small (for example, <1-µm) fat droplets are normally metabolized by endogenous enzymes, such as lipoprotein lipase and hepatic lipase. On the other hand, large-diameter (for example, >1-µm) fat globules can also be cleared from the bloodstream by cells of the reticuloendothelial system (RES), by a process known as phagocytosis, whereby they are engulfed by activated white blood cells. In addition, their malleable physical property can make them less a risk for embolism, unless of course, they are present in very large numbers. For example, when a 10-µm fat globule comes in contact with a capillary of 5-µm diameter, the normal physiologic response is an increase in pulmonary artery pressure that can force the potentially obstructive, but flexible, globule through the vessel, thereby minimizing the embolic impact.

In contrast, inflexible non-fat particles (for example, crystalline precipitates) of varying composition are generally not easily metabolized, and their clearance will often rely primarily on the RES. Moreover, their rigid structure makes them more dangerous as an embolic risk to blood capillaries and vessels, despite the body's compensatory response to facilitate their passage (for example, increase in pulmonary artery pressure). In fact, the inflexible nature of these particles can not only maximize their embolic impact, but can also cause the obstructing particles to raise arterial pressures to pathological proportions, producing, for example, pulmonary hypertension. Thus, comparatively speaking, the median lethal dose, or $LD_{50}$, of rigid particles in the bloodstream is expected to be only a small fraction of that associated with flexible fat globules. Hence, from a mechanical perspective, rigid particles are far more toxic when they are present in an intravenous injection. In a worst-case scenario, the mechanical obstruction that may occur during the intravascular administration of particle-laden injectable solutions can result in a fatal pulmonary embolism. Evidence of the human risk of intravenous exposure to rigid particles occurred approximately 15 years ago in an extemporaneously-prepared intravenous nutrition formulation containing an incompatible combination of soluble calcium and phosphate salts. As reported in an FDA Safety Alert, this formulation produced insoluble dibasic calcium phosphate crystals, causing the deaths of two patients and nearly two others from pulmonary embolisms after receiving these incompatible infusions (FDA Safety Alert, 1994).

Recognizing the pharmaceutical and subsequent health consequences of rigid particles in intravenous solutions, the U.S. Pharmacopeia imposed specific pharmacoepeial limits more than 20 years ago under Chapter <788>, entitled "Particulate Matter in Injections" (USP/NF, 2009), and the European Pharmacopeia took similar action under Chapter <2.1.19>, entitled "Particulate contamination: sub-visible particles" (EP, 2005). In contrast to the large-globule size limits set by USP <729> for injectable oil-in-water emulsions, based on the volume-weighted percentage of fat residing in over-size globules, the particle size limits set by USP <788> are based on a specific number of particles per milliliter (for example, >100 mL units) or per container (for example, ≤100 mL units) larger than two specific sizes, 10- and 25-μm. The stricter particle size limits of USP <788> presumably acknowledge the greater toxicity of large-diameter, rigid particles compared to flexible fat globules. The FDA has recently questioned whether the current limits for each size threshold specified in USP Chapter <788> are, in fact, too liberal. They have recommended consideration of a significant revision (i.e., reduction in particle count limits), based on a large body of particle size data submitted to them from injectable solution manufacturers for regulatory approval (Nath et al., 2004). These pharmacopeial limits are, however, primarily intended to avoid mechanical obstruction of blood vessels, since the particle size limits for commercially manufactured intravenous solutions are quite large (for example, 10- and 25-μm).

Beyond existing limits relating to potentially clinically important embolic globules or particles, there is substantially no other pharmacopeial oversight or recommendation regarding limits on the sizes and concentrations of particles in parenteral formulations. However, there are additional clinical risks that exist as a result of unintentionally altering the PSD and inducing instability of the dispersion, resulting in rapid agglomeration of flexible globules, or nano- or micro-precipitates in dispersions used for drug delivery. For example, in the case of drug emulsions, the droplets, liposomes or micelles are designed to carry a specific amount of drug in each delivery, or "carrier", particle. Disruptions in stability can adversely alter the otherwise homogenous distribution of the drug in the carrier particles, and growth in the mean particle size through coalescence can reduce the overall particle surface area and thus alter the dosing of the active drug in two ways. First, unstable dispersions can result in sub-therapeutic dosing by one mechanism, whereby the coalesced fraction can adhere to the walls of the infusion container, thus reducing the amount of drug available to the patient during administration. Alternatively, the coalesced particles, or droplets, may concentrate in clusters resulting in the inadvertent infusion of a bolus containing a large amount of the active drug, possibly leading to drug toxicity, especially in the case of drugs having a narrow therapeutic index (i.e., for which the therapeutic dose is close to the toxic dose). Aggregation and subsequent precipitation of particulate matter containing active ingredients can pose similar risks.

In addition, the precipitation of otherwise soluble active ingredients can in fact be accentuated by the presence of unintended "contaminant" particles, possible facilitated through the well-known process of nucleation.

There is an additional adverse health issue that can arise from the presence of smaller, non-embolic particles, posing a considerable clinical risk of harm related to the development of an allergic or immunogenic adverse reaction. These smaller particles can therefore be as dangerous as larger ones, and in some circumstances more so, wherein the particles act as an adjuvant that facilitates and/or produces an allergic reaction. The source of particulate matter may also be related to physical changes in the ingredients and/or packaging during the manufacturing process. First, to illustrate how such particles act as adjuvants in allergic reactions, it is useful to review their role, for example, in air pollution studies. In this field, airborne particle limits are classified as "$PM_{10}$", "$PM_{2.5}$" and "$PM_{0.1}$", which refer to particles having aerodynamic diameters <10 μm, <2.5 μm and <0.1 μm, respectively. When they are ingested, the immunogenic effect arising from these small diameter particles, per se, can be predicated on three main factors: 1) the nature of the particle core itself; 2) its physical properties (e.g., particle size, number/mL and surface area); and, 3) particle-bound chemical and/or metallic substances capable of eliciting an immunogenic response (Granum et al., 2002). In this case, it appears that such particles can promote an immunogenic response, whether the particles attach to airborne allergens (opsonization) and thus are "primed" (influencing both sensitization and provocation phases of the allergic response) or not, remaining unattached to allergens (Driscoll et al, 1997).

The combination of particles and allergens can result in an exaggerated allergic response, or adjuvant effect, that can progress to a potentially fatal anaphylactoid reaction in susceptible individuals. For example, in animal studies involving parenteral administration, fatal anaphylactic reactions have been observed when polystyrene particles (PSP) were combined with the model protein allergen, ovalbumin (OVA), but not when PSP or OVA were injected alone (Nygaard et al, 2005). This observation supports the synergistic, or adjuvant, effects of particulate-based antigens upon the allergic response as reviewed and described previously (Granum et al., 2002). These observations can be particularly relevant in the case of protein-based biotechnologies intended for parenteral administration, whereby the injected dispersions may contain particles inadvertently introduced either extrinsically (e.g., via manufacturing) or intrinsically (e.g., protein aggregates), producing a high adverse reaction rate, mediated in large part by immunomodulation (Giezen et al, 2008). A recent commentary from academia and federal regulators points out the current gaps in pharmacopeial standards for therapeutic protein products containing particulate matter below the size limits specified by USP <788> (Carpenter et al, 2009). However, devising a new pharmacoepial standard for all therapeutic protein products may not be possible or practical, given: a) the widely-varying chemical composition of such products; b) the widely-varying indications for use; and, c) the significant variability in the response to such exposure from the patient populations treated by these products.

For example, there currently exist numerous therapeutic protein products having widely varying chemical structures. Immunogenic reactions can be commonly associated with high molecular weight compounds containing repeating chemical groups at their molecular surfaces (i.e., epitopes), as commonly found in proteins. Some compounds are more reactive, or immunogenic, than others, a fact which can be related to structural chemical variations, unique manufacturing conditions, and the scope (for example, composition) of unintended particles generated therein. Moreover, the combination of all ingredients (both active and inactive) in a given formulation, independent of the individual components, can play a pivotal role in determining the degree of immunogenicity of the entire product. The indications for the use of therapeutic protein products, such as the route of administration (i.e., intravenous, subcutaneous, intramuscular or oral), and the frequency of administration may also be important variables affecting immunogenic potential. Finally, the uniqueness (i.e., genetic predisposition) of the patient receiving the therapeutic protein product may also contribute to the allergic response. Therefore, the immunogenicity of a given product is, not surprisingly, highly variable due to a multitude of factors. However, according to an exemplary aspect, a method is provided for achieving optimization of the PSD of the final product with respect to minimization of undesirable immunogenic effects.

Thus, the interaction between active and inactive particles is mitigated by various factors, such as the molecular weight of the active ingredient(s), the number of epitopes, the composition of inactive particle(s) and the genetic predisposition of the intended patient. The scope of typical inactive particle cores ("sterile and mobile, undissolved particles", i.e., glass, cotton fibers, "dirt", metal, plastic, rubber, etc.) found in injectables, while appearing to be rather wide-ranging, is nevertheless known, and quite finite. However, the chemical structures of biologicals appropriate for various indications can be more diverse and varied in character, and therefore so too, is the immunogenic potential of these diverse biologicals. Hence, particle limits may need to be tailor-made to avoid PSD-related adverse drug reactions for each given product, rather than established generically by devising a universally applied new pharmacopeial standard, as recently suggested (Carpenter et al., 2009).

Hence, for example, establishing a PSD signature that is well controlled and maintained during a given product's shelf life, in addition to being linked to safety and/or performance, can be of great medical consequence, as well as likely of significant economic benefit, for a wide variety of non-therapeutic applications of other commercial products and formulations.

The PSD profile and PSD signature can include either a partial representation of the total particle content of the dispersion, or a complete representation of the total particle content of the dispersion. As used herein, the term PSD refers to both partial and complete representations of the particle size distribution. In an exemplary aspect, the PSD profile and PSD signature can include a partial representation of the total particle content of the dispersion. For example, the PSD profile and PSD signature can include data for particles having a particle size of at least about 1000 nm, or at least about 100 nm, or at least about 10 nm. The particle size limits of a given PSD signature can depend on many factors, such as composition of the formulation, its application, the sensitivity of the particle sizing technique(s) employed, etc. Key regions (for example, a "sweet spot") in the PSD can be identified that are linked to product performance.

For example, the PSD profile and PSD signature can include a partial segment of the total particle size distribution which encompasses the upper particle size limit of the PSD profile or PSD signature. For example, the PSD profile and PSD signature can include a partial segment of the total particle size distribution which extends from the average mean particle size of the dispersion, to the upper particle size limit of the dispersion. In an exemplary embodiment, the PSD profile or signature is limited to containing only the partial representation of the total particle content of the dispersion, and only such partial representation is retained as the PSD profile or signature.

Use of appropriate particle size analysis instruments, spanning a size range of several orders of magnitude (for example, 0.01 to 100 micrometers), as a means of identifying the optimal PSD signature that maximizes product safety and performance, is an exemplary aspect of this disclosure.

There are several techniques for particle size analysis that in principle are able to provide, with varying degrees of absolute size accuracy and resolution, the PSD profile, and therefore may be able to identify the PSD signature for optimization of product quality and performance, as described herein. Broadly speaking, the available sizing techniques can be divided into two main categories—"ensemble" and "single-particle".

In ensemble techniques, the raw detected "signal" includes a superposition of the responses generated simultaneously by many particles, often representing a large range of possible sizes (and concentrations). The raw data is "inverted", or "deconvoluted", using an appropriate mathematical algorithm to obtain an approximation of the desired PSD. In single-particle sizing techniques, by contrast, the instantaneous detected signal is produced by only one particle. The desired PSD is obtained simply by calculating a particle size from each single-particle signal response and incrementing the accumulated particle count in the appropriate size channel of a multi-channel digital representation of the PSD. Either or both measurement methods can be used in exemplary embodiments.

In an exemplary embodiment, a single-particle sizing technique is used which can provide superior resolution of both particle size and concentration, resulting in a PSD that most closely resembles the "true" size distribution. Use of a single-particle sizing technique can be particularly beneficial, for example, for PSDs that deviate significantly from a simple, single-peak ("unimodal") distribution, instead possessing significant "structure", such as a "fat tail" of over-size particles extending well above the main population of particles. In the absence of that additional structure, the PSD could otherwise be adequately characterized by just two parameters—i.e., a mean diameter and standard deviation. The same limitation is even more evident in the case of a multimodal PSD, possessing two or more separated peaks. In measuring PSDs that have such relatively high "polydispersity", a sizing technique that is capable of providing a relatively high degree of resolution, for example, a single-particle sizing technique, can be employed in order for the details of the distribution to be accurately revealed.

An exemplary technique for characterizing many of the PSD signatures contemplated for the applications described herein is single-particle optical sizing (SPOS) technique. This technique can employ a SPOS sensor using a laser light source and associated optics to generate a thin, ribbon-like beam of light that passes through an optical flow cell, thereby defining an optical sensing zone, or "view volume", through which fluid and suspended particles pass at an appropriate, controlled flow rate. The light intensity is approximately uniform in a plane defining the cross section of the flow channel, resulting in roughly the same detector response to a particle of a given size passing through the view volume, regardless of its trajectory. The starting concentrated sample is diluted so that the particle concentration lies below the "coincidence limit" of the sensor, ensuring that sample particles in the size range of interest pass substantially one at a time through the view volume, ensuring a more accurate depiction of the true PSD.

An exemplary SPOS sensor, system and technique utilizing a combination of two known physical detection methods are described in U.S. Pat. No. 5,835,211 (Wells et al, Nov. 10, 1998), the entire contents of which are incorporated herein by reference. The first detection method is light extinction (LE), in which passage of a particle through the view volume results in a momentary reduction in the light flux passing through the flow cell and impinging on a distant LE detector. Apart from refractive index effects and assuming proper design of the optical system, the larger the particle, the larger the height of the negative-going LE pulse. The typical lower detection size limit for this LE-only response is approximately 1.0-1.5 micrometers (m), whereas the upper size limit is basically fixed by the minimum lateral dimension of the flow cell, typically 400-500 µm.

The second detection method is that of light scattering (LS), in which passage of a particle through the same view volume results in the momentary creation of a pulse of scattered light that is captured over a fixed range of (small) solid angles by a second, LS detector. The height of the resulting positive-going pulse in the LS signal also ideally increases monotonically with the particle size. Use of the LS detection method results in a significantly smaller detection size limit than what can be achieved by the LE method— typically about 0.5 µm for conventional SPOS sensors. The combined LE+LS response described in the Wells et al U.S. patent cited above results in an SPOS sensor having the merits of both an extended lower size limit and relatively large upper size limit, resulting in a typical (nominal) size range of 0.5 to 400 µm.

Improvements in the sensitivity and coincidence limit of SPOS sensors have recently been achieved using a radically different optical and signal processing approach, based on the use of a focused light beam, as described in U.S. Pat. No. 6,794,671 (Nicoli et al, Sep. 21, 2004) and U.S. Pat. No. 7,127,356 (Nicoli et al, Oct. 24, 2006), the entire contents of which are incorporated herein by reference. By design, the incident beam illuminates only a small portion of the cross section of the flow cell, resulting in detection of only a small fraction of all the particles that flow through the sensor. The intensity profile of the incident light beam is no longer approximately uniform across the flow cell, but instead it is highly focused and approximately Gaussian in shape. The resulting LE or LS signal pulse height therefore depends not only on the size of a given particle, but also on its trajectory. The resulting pulse height distribution (PHD) for particles of a given, uniform size is no longer narrow, as for an LE or LS sensor of known design, but instead is broad. Hence, in order to obtain the desired PSD, the raw PHD data can be deconvoluted to account for the different signal response produced by different particle trajectories.

The above-described focused-beam SPOS sensors possess, for example, two distinct advantages over their known conventional LE- and LS-type counterparts. First, they have significantly higher sensitivity—for example, substantially lower detectable size limits: approximately 0.6 µm for the focused-beam LE version and about 0.15 µm for the LS version. The second advantage of the focused-beam sensors is that the working particle concentration can be much higher than that of a known conventional LE or LS sensor— e.g., >1,000,000/mL for the focused-beam LE version and >10,000,000/mL for the LS version, compared to only about 10,000/mL for a known conventional sensor, whether LE- or LS-type, that utilizes a traditional "flat" light beam profile. Significantly, much less dilution of starting concentrated samples is required, thus simplifying the fluidics system required for the dilution process. Of greater practical importance is the related fact that the new sensors can be much less sensitive to the background level of particulate contamination in the fluid used to suspend and dilute the starting sample. This feature is particularly valuable when the focused-beam LS-type sensor is used to probe the lowest limits of particle size, ≤0.2 µm. A conventional known LS-type sensor would require enormous dilution of the starting sample and prodigious, time-consuming filtering of the diluting liquid in order to achieve acceptable signal/noise ratios and thus "clean", reproducible PSD results at such small particle sizes.

Another single-particle sizing technique that can be used is the "resistive pore" (or "Coulter") method. Analogous to the LE version of the SPOS technique, it is based on electrical conductivity rather than light intensity. This known method detects the momentary decrease in conductivity (for example, increase in electrical resistance) that occurs between two bodies of partially conducting fluid connected by a small aperture, through which individual particles are made to flow due to a pressure differential applied between the two fluid bodies. The height of each negative-going pulse in conductivity provides a measure of the particle volume, and hence size. This alternative technique may be less well suited than the SPOS method for determining the PSD of relatively polydisperse samples and/or especially broad PSDs.

Alternatively, an ensemble technique can be used to measure PSDs. As noted above, these sizing methods may be appropriate depending on the characteristics of the PSDs to be measured, and can be suitable for use in measuring relatively simpler (for example, unimodal, distributions). Use of an ensemble technique can, for example, lack the resolution necessary for adequately characterizing the detailed shapes of the PSD profiles and signatures contemplated herein. The most widely used ensemble technique is usually referred to as laser diffraction (LD). In reality it is based on two distinct physical principles—Mie scattering (MS) and Fraunhofer diffraction (FD). Use of the MS method is appropriate only for relatively small particle sizes—approximately 1/10 to 10 times the laser wavelength, or roughly 0.05 µm (50 nm) to several microns. It is based on the angular dependence of the laser light scattering intensity due to intraparticle interference, described by Mie theory. In general, the larger the particle size, the greater the extent of angular "dissymmetry" (forward/backward scattered intensity ratio). The intensity eventually becomes non-monotonic with increasing scattering angle. The pattern of angular dissymmetry is a function not only of the particle size, for a given laser wavelength, but also of the refractive index of the particle (relative to that of the suspending liquid), requiring knowledge of both the real and imaginary (absorption-related) components.

In practice, the MS method may be of limited usefulness when confronted with a PSD that is relatively broad, especially one that has significant "structure". As noted above, the variation of the scattering intensity with scattering angle is different for different particle diameters. These different patterns are added together, each with a weighting based on the concentration of particles for that given size, resulting in the observed variation of scattering intensity with angle. Therefore, determination of the PSD requires the measured variation of scattering intensity with angle to be "inverted", or "deconvoluted", using an appropriate algorithm. This process may be "limited" with respect to both absolute size and, especially, resolution, and therefore the MS method may not be suitable for use for characterizing some exemplary features of polydisperse PSDs, such as long, "fat" tails of over-size particles and multiple (especially closely-spaced) peaks.

A similar limitation in resolution can exist when the FD method is applied to polydisperse PSDs where the majority of particles are significantly larger than the laser wavelength (i.e., >several microns). According to ISO document 13320-1, the FD technique is effective for determining PSDs only for particles larger than 40 times the incident laser wavelength (typically 613 to 650 nm), or approximately 25 µm. In an ideal case of uniform particles, the signal response for the FD method is very simple, consisting of a set of diffraction "rings" of alternating intensity maxima and minima distributed over a range of small angles in the forward direction. The larger the uniform particles, the smaller the angular spacing between adjacent diffraction rings. In cases involving particles spanning a wide range of sizes, the diffraction intensity pattern can lose its neat periodic structure, consisting instead of a superposition of ring-like patterns of different periodicity. Determination of the underlying PSD can include the measured diffraction pattern to be deconvoluted, as in the MS method (using a different algorithm). The resulting computed PSD can possess limited resolution and also may contain serious artifacts (e.g., providing false peaks) and distortions in shape (e.g., substituting a peak for an expected long "tail" of over-size particles). Finally, a significant "blindspot" can exist between the upper effective sizing limit for the MS method (below 5 µm) and the lower effective sizing limit for the FD method. In short, single-particle optical sizing techniques can provide significant advantages in comparison with the ensemble methods of Mie scattering and Fraunhofer diffraction in measuring more complex PSD profiles and signatures.

Another (DLS), also known as photon correlation spectroscopy (PCS). Such technique can be employed at the small end of the size scale, for example, from a few nanometers to approximately 1 micrometer. The DLS technique analyzes the temporal fluctuations of the scattered (laser) light intensity caused by changes in the relative phases of the constituent scattered waves originating from each particle undergoing random-walk Brownian motion, or diffusion, in liquid suspension. As described by the Stokes-Einstein formula, the diffusion coefficient is inversely proportional to the diameter of the (spherical) particles, independent of their composition.

Quantitative information regarding the PSD can be obtained from the random fluctuations, or "noise", in the scattered light intensity detected at a particular scattering angle by analyzing the intensity autocorrelation function (ACF). The DLS technique is capable of yielding PSD results of only limited resolution. Like the MS or FD methods, DLS is an ensemble technique, in this case requiring deconvolution of the time-decaying ACF in order to obtain an approximation of the desired PSD profile or signature. The success of the deconvolution in providing an acceptable level of accuracy and, particularly, resolution, of the resulting computed PSD varies greatly with the complexity and size range of the underlying distribution. In the case of a relatively narrow "unimodal" distribution, obtaining an accurate measurement of the mean diameter and width (i.e., the standard deviation (SD), or coefficient of variation (CV)) of the PSD is straightforward. For relatively broad, asymmetric and "complex" PSD profiles which deviate from simple, unimodal distributions, the mathematical inversion techniques associated with the DLS technique may not be able to provide PSD results having the necessary resolution. Single-particle optical sizing techniques can provide advantages in comparison with such method.

In cases where there is a significant population of very small particles inaccessible by the SPOS method, including the focused-beam version—for example, smaller than about 0.15 µm (150 nm)—it may be useful to combine an ensemble technique, such as DLS, with SPOS. Such a combination can provide more useful quantitative information regarding the underlying, highly polydisperse PSD. Various sizing techniques described herein and known in the art can be used alone or in combination as tools for characterizing the desired PSD profiles and signatures for formulations.

In an exemplary embodiment, the SPOS technique, whether based on LE and/or LS designs or their newer focused-beam variants, can be employed for characterizing the PSD profiles and PSD signatures discussed in this disclosure. Such techniques can be employed, for example, both in the early stages of product formulation and also later for quality control monitoring during large scale manufacturing.

The results obtained from particle size analysis based on one or more appropriate techniques can lead to the development of a successful dispersion that ultimately possesses the desired "PSD signature". The PSD signature can possess certain particle size and concentration specifications within a defined specification. The PSD signature can serve as a target specification to be reproduced each time the formulation is made, for example, during either small- or large-scale production of the formulation. For example, failure to reproduce the PSD signature for each batch of a given product within its specified design space, which is often unique to both the manufacturing process and the composition of the product, can result in the release of inferior and/or defective final formulations. Each dispersion can have a unique set of ingredients, and therefore can also have a unique PSD signature. A defective PSD profile develops can serve as an indicator that the product is likely fail in its intended application, either producing undesirable effects or not meeting shelf-life expectations, or both. Thus, according to one aspect, a region of interest (i.e., design space) for the optimum PSD signature for a given dispersion can be identified, and such region of interest can be maintained as a manufacturing specification.

Assuming that an appropriate particle size analysis measurement yields an accurate portrayal of the PSD for a product of interest, the proposed PSD signature can be matched to the performance of a given formulation. Such a PSD signature can be applied as a principal marker or indicator of either a favorable or unfavorable product outcome. Achievement of a robust and optimized PSD signature can be verified by employing specific methods of stability testing (for example, forced accelerated degradation studies) of the dispersion. Additionally or alternatively, the composition can be reformulated in order to refine the PSD signature within narrower size and concentration limits (revised design space). This reformulation activity can also include modification of specific manufacturing steps in order to obtain the optimal design space associated with the given PSD signature. The PSD signature can be defined within specified particle size and population (for example, concentration) limits, such that it correlates with desired or optimal product performance (for example, confirming its specified design space). This approach can be useful in the case of commercial formulations for which unintended particles in suspension or solution are not well-controlled or routinely measured as part of a product-release Quality Assurance/Quality Control (QA/QC) program designed to reduce costs associated with product failure and consequent economic loss and/or to minimize public harm.

The first step in applying the concept of PSD signatures to product manufacturing can be to identify the typical PSD profile that is associated with a given successful formulation. The consistency with which the PSD profile is reproduced from one batch to the next can be determined. Depending on the processing protocol and procedures involved (for example, established Standard Operating Procedure or SOP), as well as the annual production volume for a given formulation, a statistically relevant sampling of batches can be carried out in order to establish the "current", or "typical", PSD profile. The results of such measurements can fall within the following three categories of behavior: 1) the PSD profile is consistent for all product batches and is maintained after appropriate product testing; hence, the TLT design space for the PSD signature is established and becomes a product specification; 2) the PSD profile is consistent for all batches, but the product has an unacceptably high rate of failure during stress-testing, as well as poor product performance; 3) the PSD profile is inconsistent for all batches and the product routinely fails laboratory stress assessment and field testing.

In the first scenario, an acceptable and consistent PSD profile is obtained under all testing conditions. If batches show a similar consistency under appropriate "stress" conditions, then the PSD signature and associated specifications can be written into the SOP for manufacture of the product and the PSD can be continuously monitored thereafter during production of subsequent batches to ensure that a defective product is not released. By chance, if a PSD signature associated with a defective product is encountered anytime during routine batch testing, this occurrence can signal a potential deviation from the established SOP for the product that may affect its final quality and/or performance. After confirmation of the defect in multiple replicates, a full review of the manufacturing process can be conducted in order to identify the root cause(s) of the defect. Then, appropriate changes in the manufacturing process can be made, so that either the desired PSD signature is restored or it is appropriately revised so that it falls within its specified design space, allowing batch production to be resumed and monitoring of all product batches continued.

In the second scenario, a stable or consistent PSD profile is demonstrated but falls outside the specified TLT design space after appropriate stress testing of representative samples. This occurrence can imply that, although there is consistency in the PSD profile, it does not represent the optimized PSD "signature". A stepwise review can be conducted of the manufacturing process (including, for example, analysis of raw ingredients, manufacturing conditions and packaging) of the final formulation. A review of the formulation components can also be performed, and if necessary, less reactive pharmacological agents (for example, different salt forms and alternative active pharmaceutical ingredients) or excipients (for example, buffers, antioxidants) can be considered. The specific PSD profile and the ideal formulation that maximizes product performance can be identified, thus allowing it to be adopted as the PSD signature.

In the third scenario, the entire manufacturing process can be reviewed, and ultimately likely revised, for example, in order to establish the PSD signature associated with a product that is optimized under all conditions. In extreme cases, this review process can result in the need to completely reformulate the final product. For new formulations, this tactic can be identical in scope to the procedure described under "stress conditions" above, in the sense that all processes can be reviewed and tested under realistic conditions in order to achieve a "robust", i.e. reliable, PSD profile for the formulation. Another benefit of the PSD signature can be the optimization of the various manufacturing equipment and/or processing steps used to produce a final product formulation. That is, refinement of the manufacturing procedures can be possible when guided by appropriate particle size analysis and testing conditions. Potential factors that can adversely affect particle contents in a liquid suspension, dispersion or solution can be identified and controlled, and then confirmed to favorably affect (for example, make consistent) the PSD profile within a new range of particle size and concentration limits. Appropriate accelerated stress testing can then be carried out (for example, as a final step) before adopting a revised SOP. Thus, such a procedural review can enable the formulator to refine the manufacturing equipment (for example, homogenizers, milling equipment and sterilizers) and processing conditions (for example, temperature, pressure and equipment settings) at this time, with the goal of obtaining the optimized PSD signature and its unique design space.

The final PSD profile can be stable, reproducible and closely associated with successful use of the product. The final PSD profile associated with product optimization (for example, in accordance with an established design space) becomes the "PSD signature" that in the future can determine a product batch's pass/fail condition. That PSD signature can then be uniquely applied to a particular individual product, and the design space specification can then be used as a marker of higher quality.

In the case of emulsions and suspensions, for which the PSD is associated with specific homogenization or milling procedures, a significant change from the baseline PSD or GSD over time can signal an adverse change in the quality of the dispersion.

For example, such a change may signal a conversion from the desired product, having an optimized PSD signature with a "controlled" size distribution, to an undesirable product that falls outside the specified design space, giving rise to an "uncontrolled" size distribution that deviates over time. This change can be indicative of a physically unstable or chemically incompatible dispersion, which typically would result in compromised efficacy and possibly diminished safety. If evidence of a "coarse" distribution occurs at the outset, for example, immediately following the production of a fresh batch of a given formulation, then the problem can reflect either the use of sub-optimal starting ingredient(s) or defective processing equipment and conditions, or both. Alternatively, if this deterioration in PSD profile occurs relatively slowly over the product's shelf life (for example, as the product ages over time), then the problem could be a consequence of a "subtle", undetectable defect arising from (as stated above) the raw material(s) or manufacturing condition(s), or it may be due to poorly controlled conditions during transport of the product to the consumer, unsuitable storage conditions or inappropriate application. Manifestations from a defective product can be reduced or avoided later if the appropriate accelerated stability testing procedures (Nicoli et al., 2006) and conditions are also applied at the outset, following standard testing procedures related to meeting product specifications.

In an exemplary embodiment, a solution can be produced which is "free" of particulate matter, but which, in actuality, contains a small, but "acceptable" concentration of contaminant particles, for example, low enough to minimize the risk of adverse outcomes. That is, a certain tolerable, or safe (but nevertheless unintended) population of particles (for example, insoluble active ingredients and/or extraneous particulate matter) in the PSD can be identified. The starting point can be to determine the PSD signature of such unintended particles in solution within a specified design space (for example, levels that do not produce a failure or significant harm in the application of the product).

This feature can be particularly useful for more serious safety-related adverse reactions, such as those related to immunogenicity. In this case, by discovering the ideal PSD signature (for example, size and concentration), irrespective of the actual offending agent(s), it can be possible to differentiate between a non-pathogenic PSD and a pathogenic one. This capability can be relevant in the case of biologics license applications, where a high incidence of safety problems, especially involving immunogenicity, has been documented (Giezen et al, 2008). The high rate reported in this study (23.6%) of safety-related regulatory actions can be addressed, for example, by introducing deliberately controlled PSD limitations in these formulations, as a means of protecting patients from immunogenicity-related adverse reactions. A certain PSD signature (for example, concentration vs particle size), in addition to particle load (i.e., dose), can be assured and maintained. Although the exact causes of these reactions are not fully understood, it appears that the presence of foreign particulate matter in solutions, especially in high molecular weight, protein-based formulations, may elicit a clinically significant immunogenic response. It is conceivable that a certain "condition" related to a particular PSD profile is necessary to initiate an antigen-antibody response for a given therapeutic product, which thereby produces an immunogenic reaction. Identifying the PSD signature according to an exemplary aspect can help to reduce, avoid or mitigate such adverse reactions.

Application of the concepts derived from the use of "PSD signatures", directed toward optimizing the formulation and application of liquid-based products, is briefly described herein. Methods for identifying the optimal physical characteristics of such formulations, whereby PSD profiles are generated using appropriate particle sizing techniques, is provided. Virtually all liquid-based products possess a measurable population of particles or droplets, and the relevant sizes and concentrations of greatest importance can vary with the individual product, and/or to some extent the particle size technique employed and its limits of detection. An optimal PSD signature can be desirable for yielding a safe and effective product.

A significant shift in baseline measurement of the population (for example, concentration) of particles present in a given liquid-based product can be interpreted as a change (usually degradation) in stability. It can be manifested by a significant upward shift in the number of largest-size-particles with respect to their "baseline" concentration values at time t=0 (immediately after manufacture)—for example, an "upward shift" (to larger sizes and concentration) of the large-particle "tail" of the PSD. The extent of the upward shift in the PSD depends upon the degree of physicochemical "stress" (for example, as a result of instability and/or incompatibility) existing within the formulation. In emulsions, these upward shifts in particle size and concentration in the PSD tail can be the result of particle/droplet coalescence; in suspensions, flocculation; in solutions, microprecipitation. The cause(s) can be multi-factorial and can include, for example, incompatibilities between formulation components or with the packaging materials, thereby forming insoluble products; instability of active or adjuvant ingredients, leading, for example, to the formation of protein aggregates in biological solutions; poorly controlled manufacturing conditions, resulting in extraneous particle contamination; and/or excessive temperature fluctuations occurring during transportation and/or storage.

Any significant shift in the PSD from values measured immediately following manufacturing, for example, during the course of the typical shelf-life, can be interpreted as a change in stability that can affect product performance, irrespective of where the changes occur in the PSD. Thus, in an exemplary embodiment, shifts in the PSD outside the defined design space, no matter how subtle, can be avoided.

Established commercial products can require the use of complex manufacturing processes that are able to produce on a routine basis a high quality final product. Although many formulation steps can be required in order to achieve the desired end product, the use of PSD profiles, and ultimately PSD signatures, is not included in the standard operating procedure (SOP)—for example, the methods of preparation are not controlled by a specific PSD profile. From the perspective of the PSD, such products are produced without the benefit of a routine monitoring protocol designed to control the PSD in a specific, predetermined way. By keeping the manufacturing SOP protocols "consistent", in accordance with an exemplary aspect, parameters can remain constant and "under control". For example, in the case of emulsions and suspensions, the large-diameter tail of the PSD can be closely managed within reasonable limits. Thus, by employing such PSD tail management, gross, obvious changes (for example, irreversible phase separation) can be reduced or avoided in the final formulation. A characteristic PSD signature (for example, one having a specific shape in terms of the number of particles per unit volume for each particle size within a specific range), for example, that is reflective of the unique processing steps required to manufacture the product (in addition to its composition), can be monitored and controlled during production. By employing such PSD signature, an effective, stable and safe final product can be attained.

According to an exemplary aspect, a method can include: 1) identification of the optimal composition of ingredients that influence key regions in the PSD and that may be important features of the formulation related to the type, number and concentration of particles present; 2) establishing a particular PSD profile that is consistently produced from batch to batch; 3) establishing the boundaries of such a PSD profile within pre-defined acceptable limits; 4) establishing the optimal PSD signature for a given formulation that determines the final specification for batch release. A stepwise approach as indicated above can, for example, identify the best combination of ingredients and particle limits that yield the optimal PSD signature for a given formulation.

Regarding the first step above, the composition of the particles that contribute to the measured PSD profile can be identified in order to determine the factors contributing to their formation and stability against agglomeration. In oil-in-water emulsions, for example, the enlarged fat globules residing in the GSD "tail", resulting from coalescence of smaller droplets, can include oil and emulsifier, but they may also contain ionically-active adjuvant components that are either intrinsically present in the formulation or released from its packaging container. Knowing the role of these additional components that circulate around, adsorb onto or penetrate into the globules can reveal the cause behind the abnormalities that appear in the PSD. This knowledge, in turn, can suggest the most appropriate remedial measures for restoring the PSD profile to its desired structure (i.e., boundaries, particles/mL and shape).

Another example is a protein-based solution, for which a similar approach would be to identify the abnormal presence of particles that deviate from the desired PSD profile of these formulations, which, together with the composition of the particles, can assist in identifying the corrective action(s). The type of particles that contribute to its profile under typical manufacturing conditions can be determined. Analytical techniques such as, for example, microscopy, FTIR and gas chromatography/mass spectroscopy, can be employed to identify the abnormal particles. Knowing their physical and chemical makeup, and separating the sub-populations of "intended" and "unintended" particles, can help to suggest certain manufacturing steps that may be corrective. For example, identifying unintended particles can result in altering a processing step that reduces or removes them from the final product, thus producing a more favorable PSD profile for a given formulation.

Regarding the second step above, finding a PSD profile that is consistently produced can be desirable. At times, more than one PSD profile can be shown to be consistently produced from different manufacturing steps, and different numbers and types of ingredients in a proposed formulation. The formulator can first determine the ideal sets of ingredients for potential formulations, and then assess the results based on the PSD profile(s) obtained. Achieving consistent PSD profiles may, for example, include several qualitative reviews, involving varying the ingredients of the formulation, the processes by which the product is manufactured, its packaging container and the storage conditions. In the case of the ingredients, for example, the quality of the raw materials containing the active ingredient(s) can be investigated, possibly resulting in revision of the specifications that accompany the certificate of analysis for each ingredient. Similarly, the composition and concentration of excipients (for example, antioxidants, preservatives, buffers, solvents and salts) in the formulation can include additional review in order that they be consistent with the revised specifications. This review can result in substitution of certain excipients by others that continue to perform the desired function, but which produce a consistent PSD profile from a series of batches. In this way, the ingredients and processing steps can be standardized to a specific PSD profile that is unique to the product. These actions can, in turn, result in a reformulation of the product, which can limit the number of approved suppliers and/or options for each ingredient in order to achieve an acceptable PSD profile.

Regarding the third step above, once a consistent PSD profile (i.e., shape) is achieved on a routine basis, the question is whether it can be controlled within certain boundaries can be explored. The resulting PSD profile can resemble a simple unimodal in shape or, instead, a bimodal or more complex, multimodal distribution. The acceptable statistical boundaries (variances) for such a profile can be established, whether it is very narrow or quite broad, and whether or not the PSD is reproducible. The PSD profile that is most consistently produced might not necessarily correspond to a more stable product. That is, once the best combination of ingredients and processing conditions is determined, the PSD profile of the final formulation can then be tested under various "stress conditions". This latter aspect can be answered by the use of stability assessments, for example, using the methods for accelerated stability assessment described in U.S. Pat. No. 7,150,996 (Nicoli et al), the entire contents of which are incorporated by reference herein, in order to evaluate the robustness of the proposed PSD profile in terms of its ability to confirm the resistance to changes due to coalescence, flocculation, aggregation or precipitation. This systematic approach can correlate a consistent PSD profile with both normal (unstressed) and stressed conditions in order to establish the robustness of the distribution under variable conditions.

Regarding the fourth step above, the PSD profile can then be matched against some pre-defined performance conditions. In order to be considered a candidate for the final PSD signature, the PSD profile can be shown to correlate well with favorable product performance. As long as the concentration of active ingredients and excipients do not change and the PSD does not worsen relative to pre-existing PSD profiles (for example, does not fall outside certain boundaries, remaining "compatible"), the testing conditions at this stage can be relegated primarily to the determination of shelf life and application-related assessments. If, however, achieving the perceived optimal PSD signature requires significant corrective actions, including re-formulation of the product, as previously discussed, then the earlier testing steps can be repeated. In the case of a medicinal product, the level of testing required can be determined by the FDA, through a new drug application (NDA). By employing such PSD profile, acceptable products can be identified that can be made in a reproducible manner and withstand certain conditions associated with stress testing. The PSD signature, having been verified as described above to be within the design space for a given product, can serve the function of confirming desired or optimal properties of the final product with respect to its stability, compatibility and efficacy, and/or safety.

According to an exemplary aspect, a method is provided which includes: (1) characterizing and/or identifying the PSD, (2) determining the batch-to-batch consistency of the PSD, (3) defining the boundaries of the PSD profile, (4) performing an accelerated assessment of the stability of the PSD profile, and (5) establishing the PSD signature as a benchmark.

In order to illustrate some of the aforementioned concepts involving PSD (or GSD) profiles and signatures, GSD profiles of several different oil-in-water injectable emulsions emphasizing the "tail" of over-size oil globules (diameter>1.8 µm) are shown in FIGS. 1-10. These results were obtained using the SPOS technique (LE method) as described above, which is insensitive to the vast number of oil droplets smaller than the measurement threshold of 1.8 µm, comprising the majority of the overall droplet/globule distribution. In these examples, this outlier tail region of the GSD was selected for investigation, as it is can be the most important in terms of correlating with the stability and safety of injectable emulsion products.

The plots depicted in FIGS. 1, 3, 5, 7 and 9 show the particle, i.e., globule concentration, expressed in number of globules/mL, for the starting, undiluted sample suspension, obtained from the "raw" SPOS particle-count results (for diluted samples). The plots depicted in FIGS. 2, 4, 6, 8 and 10 show the volume fraction distribution, or VFD, of the large globules for the corresponding samples shown in the odd-numbered Figures, expressed as a percentage of the total oil (fat) concentration in the starting, undiluted samples. The volume fraction values are computed from the globule concentration values shown in the corresponding odd-numbered Figures, recognizing the spherical form of the dispersed globules in these formulations.

The GSDs shown in FIG. 1 were obtained from three commercial products made by Manufacturer "A" having similar composition but different percentages of oil in the dispersed phase—10% (open circles), 20% (open triangles) and 30% (open squares) oil (w/v). As can be seen from FIG. 1, the profiles of the GSDs, expressed as number of globules/mL in the undiluted sample suspension, are reasonably similar for the 10% and 20% oil emulsions—roughly 40,000-70,000/mL in the size range 1.8-5 µm, with a steep drop to much smaller values above 5 µm. By contrast, the globule concentration values for the 30% oil emulsion are much higher in this size range, varying between 150,000 and 225,000/mL. While the globule concentration also drops precipitously above 5 µm, the "outlier tail" remains significantly elevated relative to the tails observed for the 10% and 20% emulsions in the range of 5-10 µm and beyond.

Figure 2:
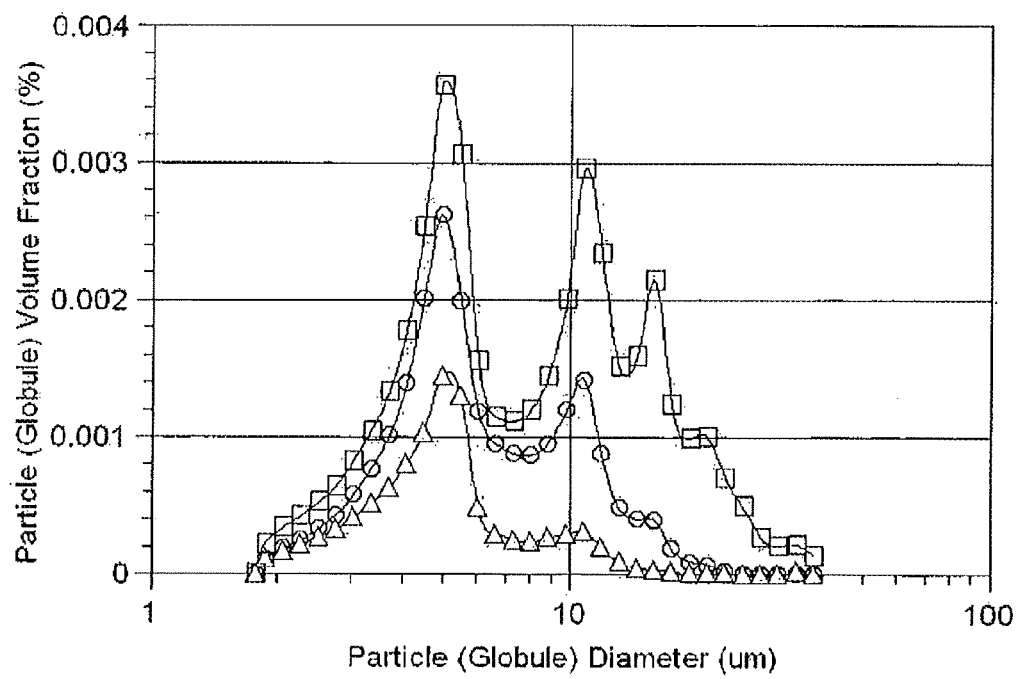
FIG. 2 is a graph showing globule volume fraction (%) vs. diameter (μm) corresponding to the three plots shown in FIG. 1 for oil concentrations (w/v) of 10% (open circles), 20% (open triangles) and 30% (open squares), according to an exemplary aspect.

FIG. 2 shows the VFD plots for the three emulsions, corresponding to the GSDs shown in FIG. 1 (same symbols for the three oil concentrations). There is considerable "structure" observed in the VFDs. Whereas the GSDs for the 10% and 20% oil emulsions are seen to be fairly similar when expressed as particles/mL in FIG. 1, the same is not the case for the corresponding VFDs shown in FIG. 2. The VFD for the 10% oil emulsion (open circles) exhibits two pronounced, descending peaks, centered at approximately 5 µm and 11 µm. In addition, there is a suggestion of a peak at approximately 15 µm, followed by a smooth decline in volume fraction. These sizes and all others listed hereinafter are approximate, provided for illustrative purposes only. The VFD for the 20% oil emulsion (open triangles) might be expected to be similar, but somewhat higher in absolute values, to that obtained for the 10% oil emulsion, based on the GSD results shown in FIG. 1. However, this is not the case. The VFD for the 20% oil emulsion retains the peaks centered at 5 µm and 11 µm, with no additional peaks beyond this range. Moreover, the absolute values of the VFD are substantially lower than those seen in the VFD for the 10% oil emulsion. Finally, the VFD for the 30% oil emulsion more closely resembles the VFD found for the 10% oil emulsion, showing prominent peaks at the same 5 µm and 11 µm locations, as well as a clear peak at 15 µm.

Not surprisingly, the entire "structure" of the VFD for the 30% oil emulsion is significantly elevated relative to the VFDs found for the 10% and 20% oil emulsions. However, what is surprising is the "reversal" observed in the maxima of the volume fraction values—i.e., 30%>10%>20%—compared to the order "expected", and seen, for the GSDs based on the number of globules/mL (FIG. 1): 30%>20%>10%. Finally, these particular formulations exhibit unique structures that are specific to the manufacturer and show a propensity for multiple peaks in the tail of the GSD. Specifically, as the emulsion coarsens (i.e., the 10% and 30% formulations), a third peak emerges in the extreme tail of the GSD at approximately 15 µm.

The differences in shape and absolute values seen in the GSDs and corresponding VFDs summarized above confirm the concept that these plots can be thought of as "fingerprints" of the respective products. The GSDs and VFDs show clearly different profiles for oil emulsions that are similar in composition (apart from oil concentration) and end use. Some of these products may be more prone to colloidal instability and premature product failures and/or safety-related issues than others, suggesting that identification of an optimal PSD, or GSD, signature may be useful.

Figure 3:
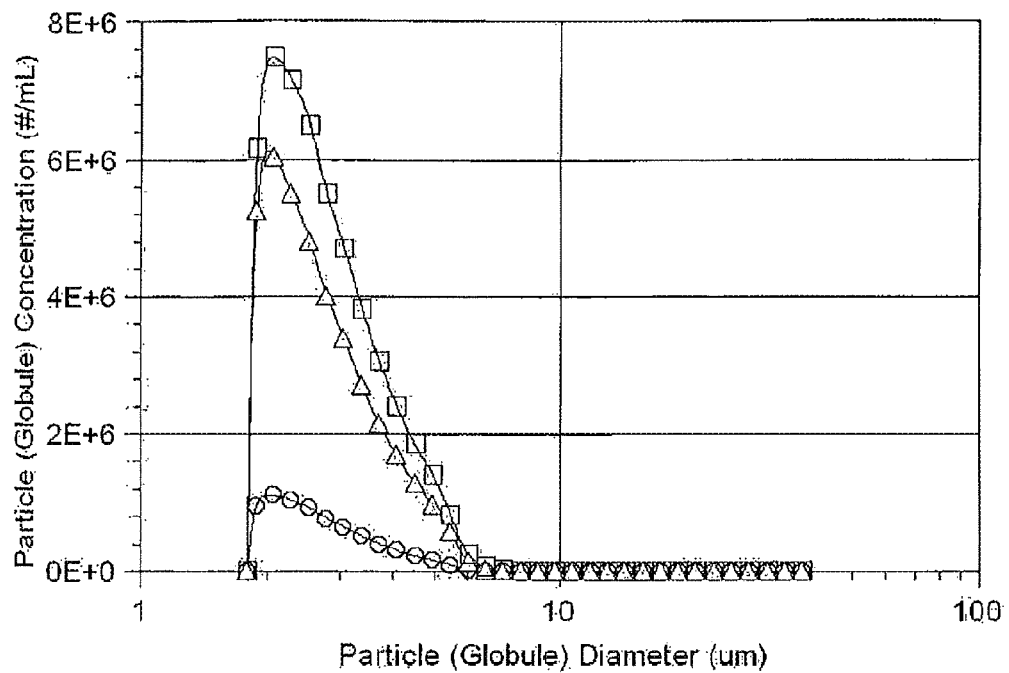
FIG. 3 is a graph showing a particle size distribution profile, globule concentration (number of globules/mL) vs. diameter (μm), obtained by SPOS for o/w emulsions (Manufacturer "B") having oil concentrations (w/v) of 10% (open circles), 20% (open triangles) and 30% (open squares), according to an exemplary aspect.
Figure 4:
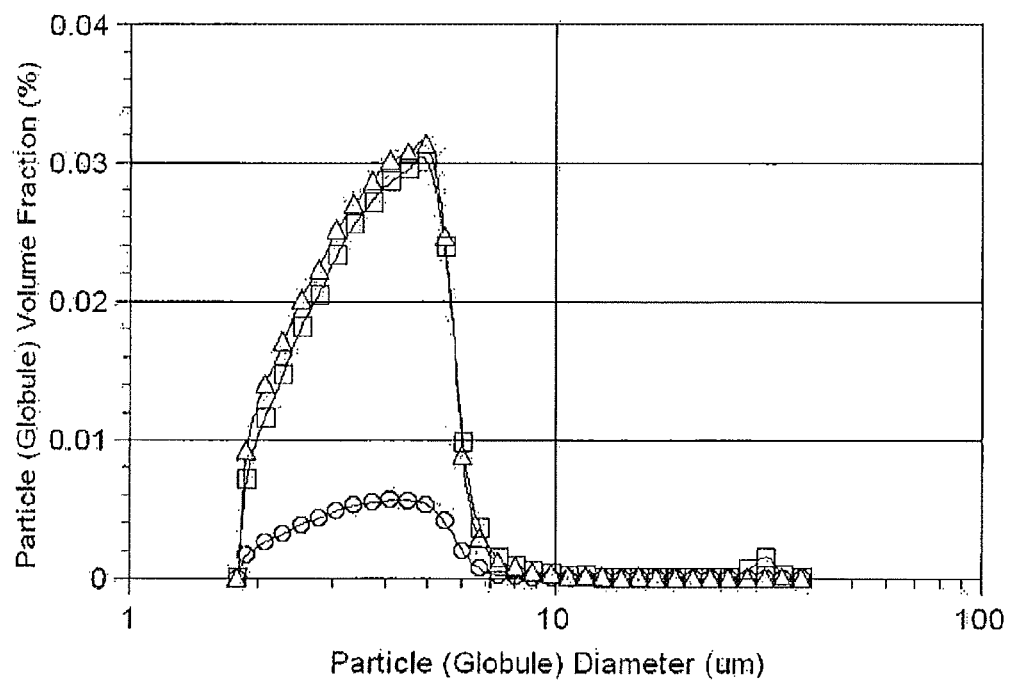
FIG. 4 is a graph showing globule volume fraction (%) vs. diameter (μm) corresponding to the three plots shown in FIG. 3 for oil concentrations (w/v) of 10% (open circles), 20% (open triangles) and 30% (open squares), according to an exemplary aspect.

FIGS. 3 and 4 show, respectively, the GSDs and VFDs obtained for three oil emulsions made by Manufacturer "B", similar in composition to those of Manufacturer "A". As before, the emulsions differ by oil concentration: 10% (open circles), 20% (open triangles) and 30% (open squares). As seen in FIG. 3, the GSD "profiles" observed for these three emulsions are significantly different in both shape and absolute value than the corresponding profiles shown for the "A" emulsions in FIG. 1. First, in each case the globule concentration (number/mL) vs diameter displays a smooth, monotonic decay from 2 µm to 10 µm, with no steep drop/inflection seen at 5 µm, in sharp contrast to the shapes seen for the "A" profiles. Second, the maximum (at 2 µm) concentration values are much larger (by at least an order of magnitude) for the "B" emulsion—1,000,000/mL vs. 40,000/mL for the 10% oil emulsions, respectively; 6,000,000/mL vs. 70,000/mL for the 20% oil emulsions, respectively; and 7,500,000/mL vs. 225,000/mL for the 30% oil emulsions, respectively. Third, the similarities, or relationships, among the three "B" GSDs are very different from those found for the "A" emulsions. Here, the maximum concentration increases 6-fold (instead of only 1.5-fold) in going from 10% to 20% oil. There is then only a relatively small further increase in going from 20% to 30% oil, compared to the almost 4-fold increase for the corresponding "A" emulsions. In the case of the "A" emulsions, the 10% and 20% emulsions showed similar GSD profiles (concentration), whereas for the "B" emulsions, the 20% and 30% emulsions have similar profiles.

The remaining differences in the profiles of the "A" and "B" emulsions are revealed by the two sets of VFDs. First, there is a significant difference in the magnitudes of the volume fraction values. The GSD maxima were seen above to be much larger for the "B" emulsions than for their "A" counterparts. Hence, it is not surprising that the maximum volume fraction values found for the three "B" emulsions (FIG. 4) are roughly 10 times those observed for the "A" emulsions. Second, there are major differences in the shapes of the VFDs. In the case of the "B" emulsions, the shapes of all three VFDs resemble broad, smooth unimodal (albeit asymmetric) distributions. This behavior is in sharp contrast to the multi-peaked shapes observed for the "A" emulsions. The remaining difference in profiles for the two sets of emulsions concerns the similarities, or lack thereof, among them. In the case of the "B" emulsions, the VFDs found for the 20% and 30% oil emulsions are nearly identical and larger by 3-fold in (maximum) absolute value than the 10% emulsion. However, this comparative ordering of the volume fraction profiles and absolute values could have been approximately predicted by the large differences in the GSD concentration values as depicted in FIG. 3. Again, it is clear that the shapes and absolute value behavior seen in the VFDs for the "B" emulsions are fundamentally different from those found for the "A" emulsions. As noted for the "A" emulsions, the differences in shape and absolute values of the GSDs and corresponding VFDs summarized above confirm the concept that these plots can be thought of as "fingerprints" of the respective products, now extended to also reflect the different manufacturers.

Figure 5:
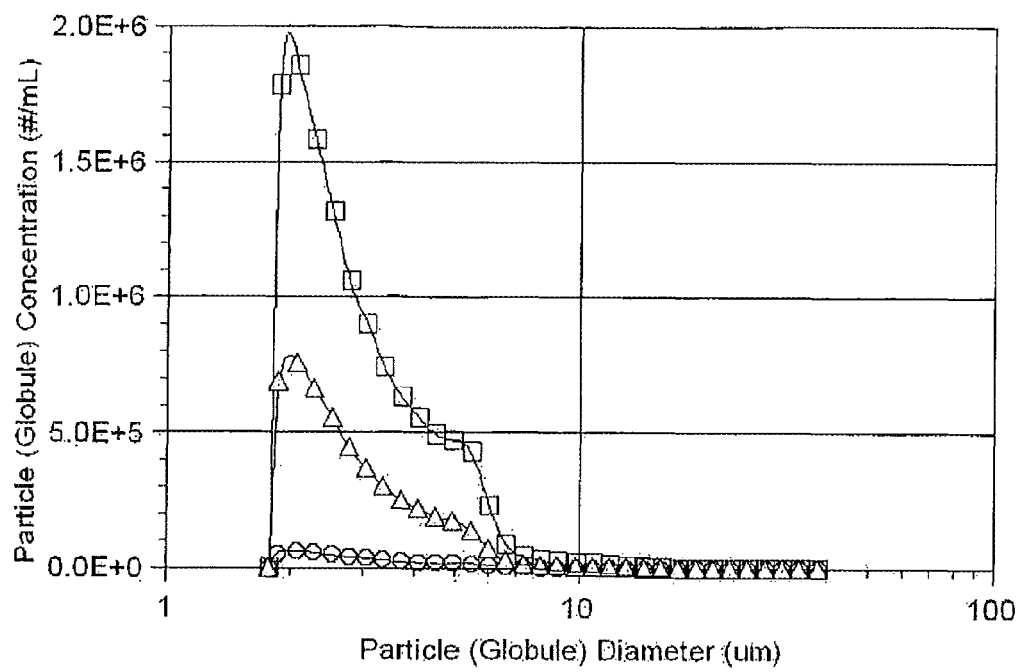
FIG. 5 is a graph showing a particle size distribution profile, globule concentration (number of globules/mL) vs. diameter (μm) obtained by SPOS for o/w emulsions (Manufacturer "C") having oil concentrations (w/v) of 10% (open circles), 20% (open triangles) and 30% (open squares), according to an exemplary aspect.
Figure 6:
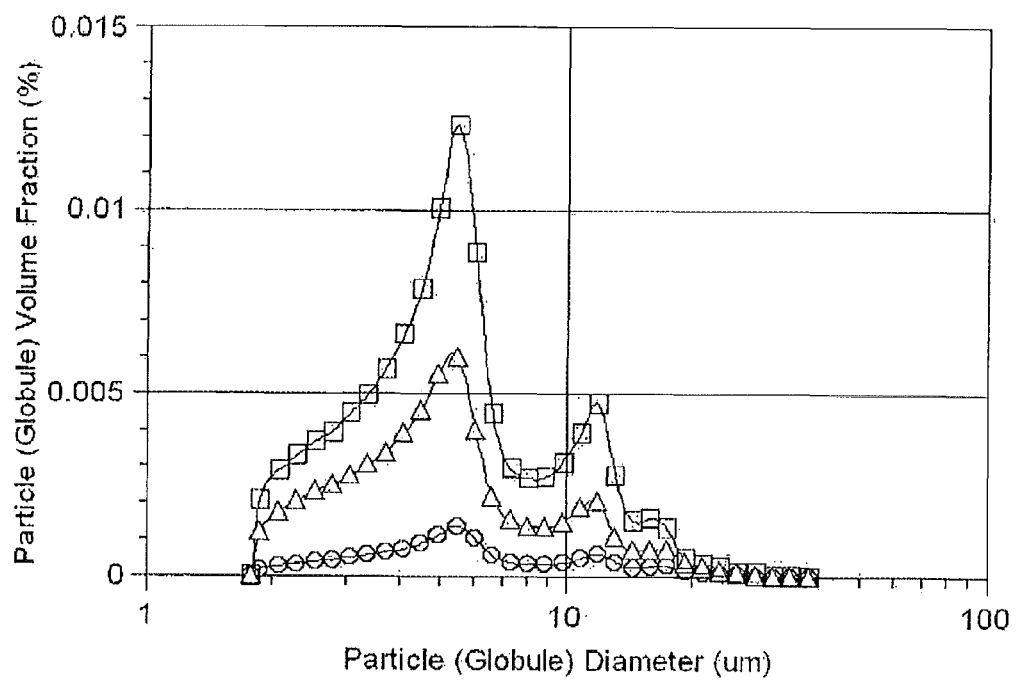
FIG. 6 is a graph showing globule volume fraction (%) vs. diameter (μm) corresponding to the three plots shown in FIG. 5 for oil concentrations (w/v) of 10% (open circles), 20% (open triangles) and 30% (open squares), according to an exemplary aspect.

FIGS. 5 and 6 show, respectively, the GSDs and VFDs obtained for three oil emulsions made by Manufacturer "C", again similar in composition to the "A" and "B" emulsions. As before, the emulsions differ in oil concentration: 10% (open circles), 20% (open triangles) and 30% (open squares). As seen in FIG. 5, the GSD profiles obtained for the three emulsions again differ significantly in both shape and absolute value from the corresponding profiles obtained for both the "A" and "B" emulsions, occupying an "intermediate position" relative to both. First, the globule concentration (number/mL) vs diameter plots are more similar in shape to those of the "B" emulsions, having a smooth, monotonic decay from 2 μm to 10 μm, with a noteworthy drop/inflection seen at 5 μm only for the 30% oil emulsion. Second, the three GSD tails are spaced more uniformly apart in concentration, where the maximum value (at 2 μm) is very small (60,000/mL) for the 10% oil, moderately large (760,000/mL) for the 20% oil and very large (1,860,000/mL) for the 30% oil.

Again, these maximum values lie between those of the "A" and "B" emulsions.

The remaining differences in the profiles of the "C" emulsions relative to those of the "A" and "B" emulsions are again revealed by the VFD plots, shown in FIG. 6. These plots reveal the multi-peak behavior that closely resembles the VFD profiles seen for the "A" emulsions, with prominent peaks located at approximately the same positions in the volume-weighted tail of the GSD for all three oil concentrations. There are two differences worth noting between the "C" and "A" VFD profiles—one quantitative, and the other qualitative. The quantitative difference is that the maximum (peak) volume fraction values found for the "C" emulsions are almost four times the maximum values obtained for the "A" emulsions. The qualitative difference is that in the case of the "C" emulsions there is a monotonic increase in the peak volume fraction values (for both prominent peaks at the 5 μm and 11 μm locations) with increasing oil concentration. Indeed, the VFD plots are clearly and significantly separated, as seen in FIG. 6. In contrast, the volume fraction values for the "A" emulsions are reversed (i.e., decreasing) in going from 10% to 20% oil, as noted above. As noted for the emulsions in the "A" and "B" series, the differences in shape and absolute values seen in the GSDs and corresponding VFDs summarized above confirm the concept that these plots can be thought of as "fingerprints" of the respective products, and more clearly they can now be extended to also reflect the different manufacturers.

Figure 7:
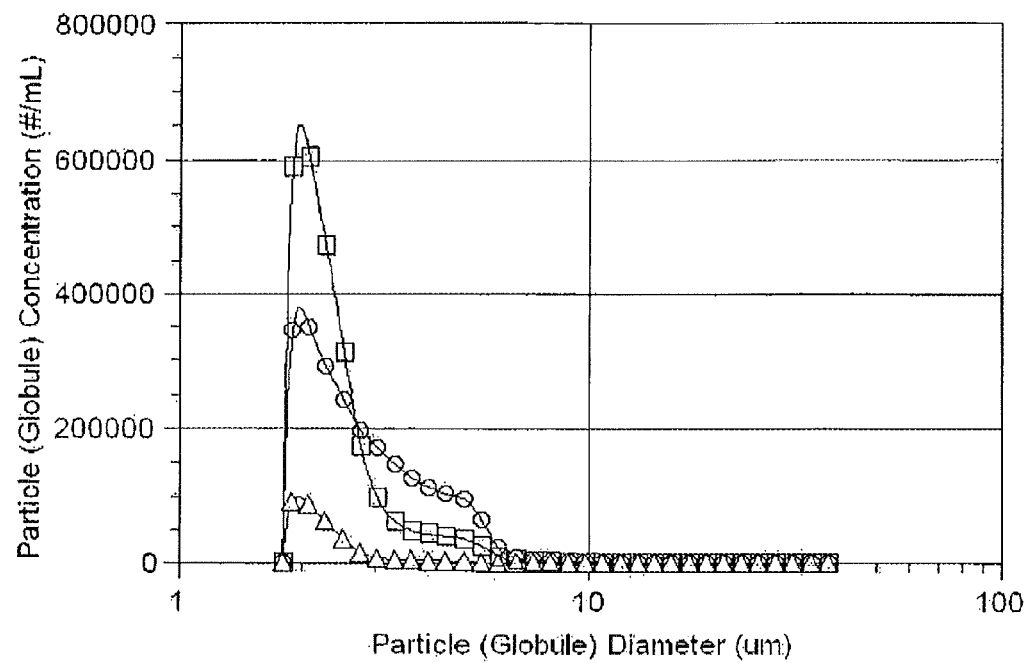
FIG. 7 is a graph showing a particle size distribution profile, globule concentration (number of globules/mL) vs. diameter (μm) obtained by SPOS for o/w emulsions (Manufacturer "D") having oil concentrations (w/v) of 10% (open circles), 10% (open triangles) and 20% (open squares), according to an exemplary aspect.
Figure 8:
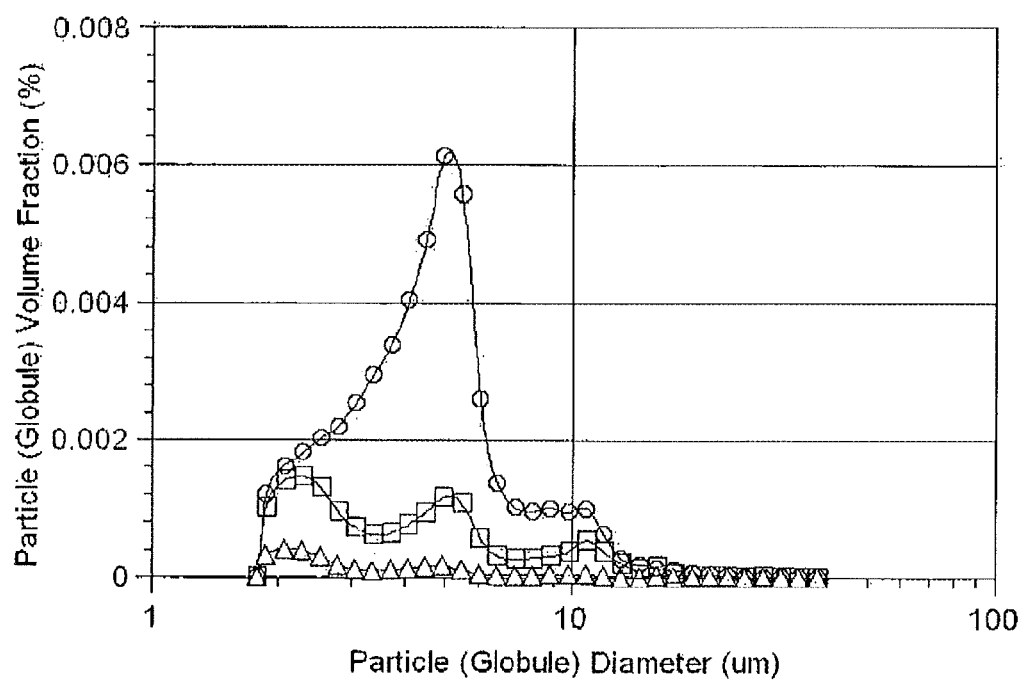
FIG. 8 is a graph showing globule volume fraction (%) vs. diameter (μm) corresponding to the three plots shown in FIG. 7 for oil concentrations (w/v) of 10% (open circles), 10% (open triangles) and 20% (open squares), according to an exemplary aspect.

FIGS. 7 and 8 show, respectively, the GSDs and VFDs obtained for three oil emulsions made by Manufacturer "D". In this case, two emulsions contained 10% oil (open circles and open triangles) and the third contained 20% oil (open squares). As seen in FIG. 7, the GSD "profiles" observed for the three emulsions again differ significantly in both shape and absolute value relative to the corresponding profiles obtained for the "A", "B" and "C" emulsions (10% and 20% oil). First, there is a major difference in the GSD tails found for the two 10% oil emulsions. Both show a smooth, monotonic decay from 2 μm to 10 μm, with the familiar drop/inflection seen at 5 pm only for first 10% oil emulsion (open circles). However, the second 10% oil emulsions (open triangles) exhibits a much smaller tail of large globules—maximum concentration (at 2 μm) of 100,000/mL compared to 350,000/mL for the second 10% oil emulsion. Second, the profile obtained for the 20% oil emulsion (open squares) differs significantly in shape from the GSD profiles found for the two 10% oil emulsions. The fact that its maximum concentration (at 2 μm), approximately 600,000/mL, is almost twice the value found for the first 10% oil emulsion is one feature. A notable difference in its profile is the much steeper (faster) decay in concentration with increasing globule diameter: the globule concentration drops to one-sixth of its maximum value in going from a globule size of 2 μm to only 3 μm. As a result of this uncharacteristically steep drop, there is an unusual "crossover" that occurs between the fast-decaying GSD profile of the 20% oil emulsion with the more slowly decaying GSD profile of the first 10% oil emulsion.

The corresponding VFD plots shown in FIG. 8 highlight prominent differences in the profiles of these three "D" emulsions from a volume fraction perspective. First, the volume fraction values for the first 10% oil emulsion (open circles) greatly exceed the values for the other two emulsions, especially the second 10% oil emulsion (open triangles). Second, the VFD plot for the 20% oil emulsion (open squares) (and to a lesser extent the plot for the second 10% oil emulsion) exhibits multi-peak behavior seen previously for the "A" and "C" emulsions.

Figure 9:
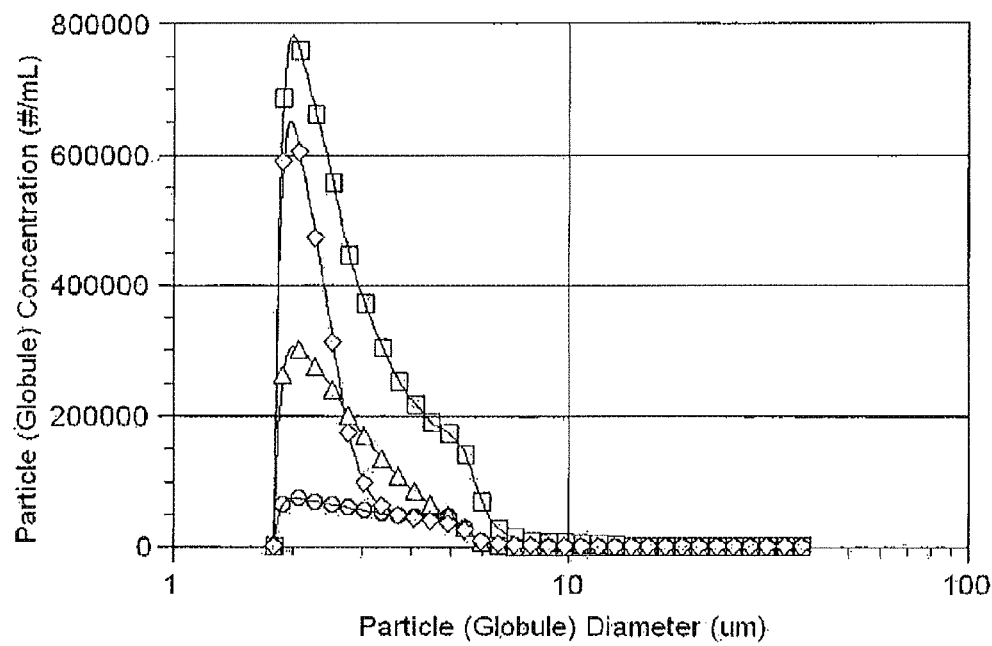
FIG. 9 is a graph showing the particle size distribution profile of the 20% o/w emulsions made by Manufacturer "A" (open circles), "B" (open triangles), "C" (open squares) and "D" (open diamonds), according to an exemplary aspect.
Figure 10:
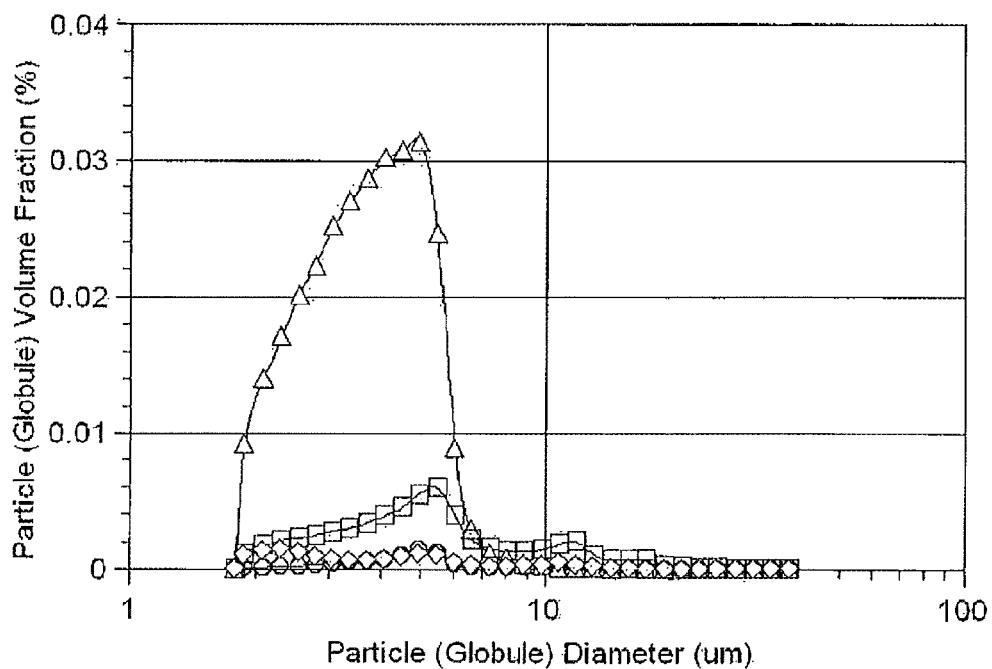
FIG. 10 is a graph showing the globule volume fraction (%) vs. diameter (μm) plots corresponding to the GSDs shown in FIG. 9 for the 20% o/w emulsions made by Manufacturer "A" (open circles), "B" (open triangles), "C" (open squares) and "D" (open diamonds), according to an exemplary aspect.

FIGS. 9 and 10 summarize, respectively, the GSD profiles and corresponding VFDs for the 20% oil emulsions made by Manufacturers "A" (open circles), "B" (open triangles), "C" (open squares) and "D" (open diamonds), as discussed individually above. The plots in FIG. 9 highlight the similarities in shape (smoothly decaying), but significant differences in magnitude (# globules/mL), of the GSDs obtained for the four different examples of 20% oil emulsions. The corresponding plots in FIG. 10 show the dominance of the "B" 20% oil emulsion in absolute volume fraction relative to the other three 20% examples, especially "A", "C" and "D". These significant differences in the GSD and VFD profiles for oil emulsions of very similar composition and constituent concentration that would have been expected to be similar, serve to highlight structural differences between the various manufacturers' products.

The consequences of not producing a consistent PSD profile in these cases seem more obvious with respect to quality control, or the lack thereof. Intuitively speaking, the profile with the narrowest or "leanest" large-diameter tail (for example, extending out the least to larger globule diameters) in these examples would ostensibly be the most stable (see "A" in FIG. 2), but in fact, in separate investigations of these emulsions, this turned out not to be the case. This counter-intuitive result points out the benefit of performing physical and/or chemical accelerated stress testing, in addition to the need to carry out appropriate particle or globule size analysis, in support of arriving at an optimal PSD signature.

The variabilities between the products with respect to their large-diameter GSD "tails" discussed above can be attributable solely to the four different manufacturing processes, since the formulations depicted are of similar composition. The detailed differences in the shapes and extent (maximum size) of the GSD tails obtained for these four formulations would suggest that products made by Manufacturers "B" and "C" would be the most likely to fail under any condition (stability, compatibility, efficacy and/or efficacy), due to the "inconsistency" and apparent coarseness of the GSD profiles from one batch to another. By contrast, products made by Manufacturers "A" and "D" would normally be thought to be more resilient and therefore better overall formulations, because their large-globule "tails" are less coarse from batch to batch. Possibly of even greater concern is the fact that, despite the consistencies observed between formulations "A, B and C", which are of nearly identical composition, their respective PSD profiles and corresponding stabilities under the same stress conditions are very different. These findings emphasize an important distinction between "quality" and "stability", where the conventional view would correlate the two, but, in fact, such is not necessarily the case. Rather, it appears that manufacturer-specific conditions surpass the conventional wisdom that presently tends to correlate the two conditions. It can be beneficial to apply stress conditioning through the establishment of a specific PSD signature to achieve the optimum stability of a given formulation.

Figure 11:
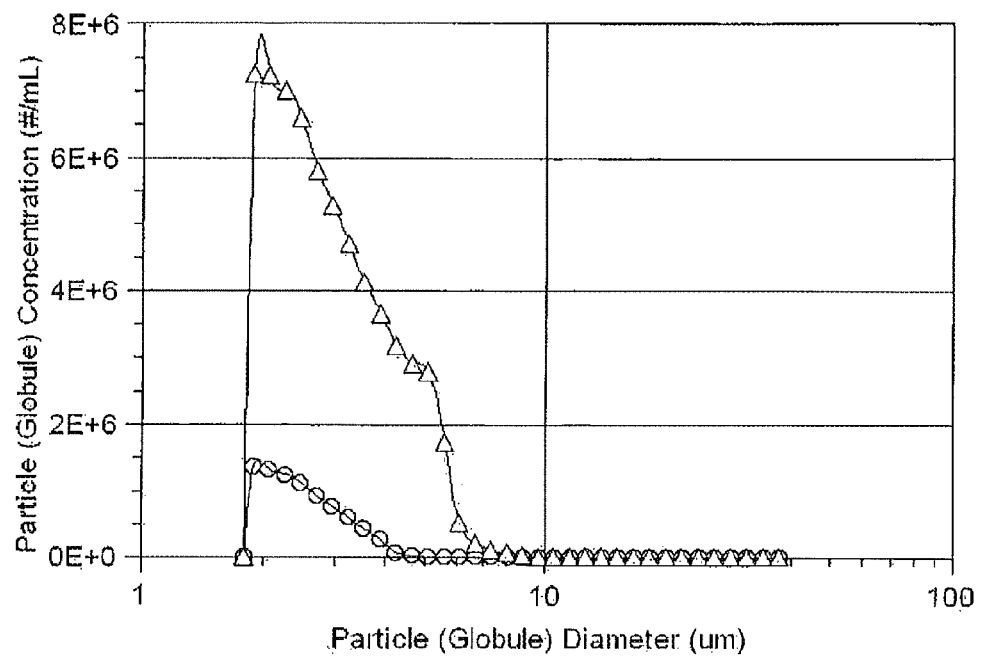
FIG. 11 is a graph showing a particle size distribution profile, globule concentration (number of globules/mL) vs. diameter (μm) obtained by SPOS for 20% o/w emulsions made by a particular manufacturer before reformulation (open triangles) and after (open circles), according to an exemplary aspect.
Figure 12:
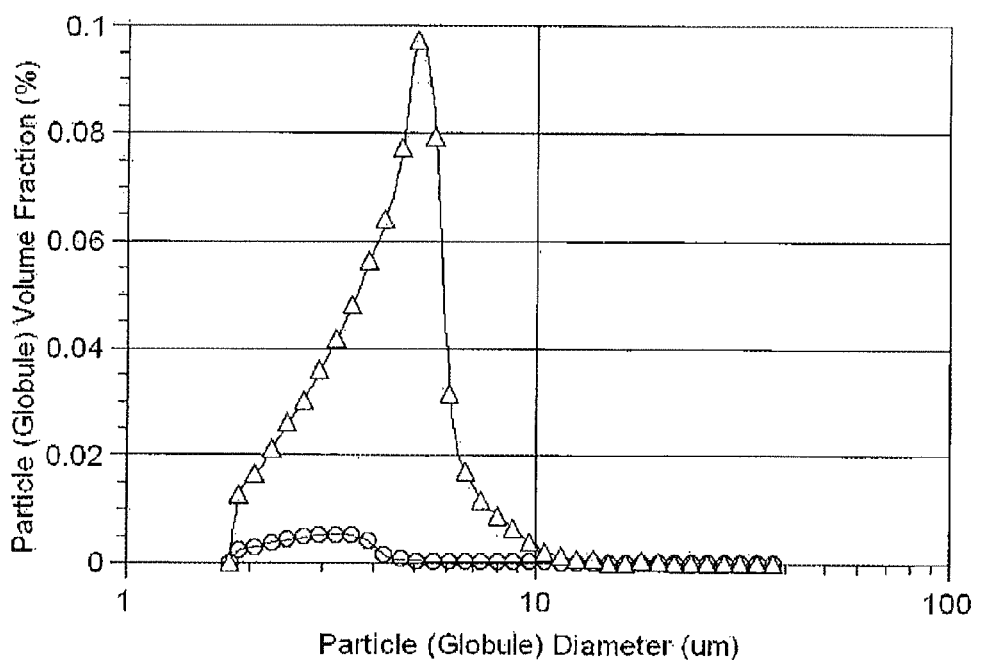
FIG. 12 is a graph showing globule volume fraction (%) vs. diameter (μm) corresponding to the two GSD plots shown in FIG. 11 for 20% o/w emulsions made by a particular manufacturer before reformulation (open triangles) and after (open circles), according to an exemplary aspect.

There is an example of the major consequences that resulted from the decision of an o/w emulsion manufacturer to change its packaging container from a conventional glass bottle to a newly developed plastic container. The new emulsions contained in plastic bags were shown to be significantly coarser (i.e., having larger, more extensive GSD tails) than the older emulsions contained in conventional glass bottles. Once this defect was realized, the manufacturer successfully reformulated the emulsion in plastic containers so that it was pharmaceutically equivalent to the original product. FIGS. 11 and 12 summarize, respectively, the GSD profiles and corresponding VFDs for different representative batches of a 20% oil emulsion produced in plastic bags before reformulation (open triangles) and after reformulation (open circles) to correct the problem. The plots in FIG. 11 highlight the significant differences observed in both shape (smoothly decaying) and magnitude (# globules/mL) of the GSDs. The corresponding plots in FIG. 12 show the dominance of the "coarse" version of the 20% oil emulsion in plastic before reformulation, based on its absolute volume fraction, relative to the "fine" product after reformulation. The GSD (FIG. 11) and VFD (FIG. 12) profiles for these identical oil emulsions would normally be expected to be "similar" in every respect. However, the large differences highlight the major qualitative changes that unexpectedly occurred as a result of "simply" changing the container. In this example these qualitative differences were subsequently shown to correlate strongly with adverse changes in stability, i.e., the coarse emulsion was shown to be significantly less stable than the fine one.

The foregoing examples serve to illustrate the significance of the occurrence of particles or droplets/globules in various dispersions or solutions as they relate to the final properties, efficacy and possibly safety of products containing them, and possible adverse consequences in the absence of monitoring and controlling the PSD. The PSD associated with any liquid particle dispersion or solution possesses "tolerable limits" within a specific product design space. As described previously, the latter phrase, as used in this disclosure, refers to the concentration (number per unit volume) of particles or droplets/globules and/or the VFD that is present over a given particle size range for any final liquid formulation, and existing throughout its shelf life, that is not associated with adverse performance (for example, efficacy) or safety during use. A unique TLT design space for a given PSD can exist for all liquid formulations, irrespective of their composition or use. Furthermore, a deviation from this design space can cause the final product to fail—in some cases with serious economic consequences or severe health effects. The concentration of particles of given sizes that define the design space of a given product, and which therefore are not to be deviated from, can vary with the formulation and the manufacturer. However, the factors affecting the final PSD can be controlled in order to avoid formulations containing an abnormal population of particles of certain sizes that cause the final product to fail in its intended use. In the present disclosure, identifying the boundary between tolerable and intolerable particle concentration values (for any given PSD) is an important goal in establishing peak product performance. The ideal shape of a PSD, and therefore the optimal PSD signature, cannot be assumed by the "relative" fineness or coarseness of the formulation, but can only be obtained by matching the PSD to product stability and performance. An optimal PSD signature can be identified for a given formulation or final product that is most closely associated with the successful performance of that formulation or final product. The PSD signature, therefore, can also be useful in identifying the cause(s) behind product failures.

Formulation factors that can affect the performance and characteristics of final products can include, for example, raw materials, active ingredients, stabilizers, preservatives, methods of preparation, machinery, packaging container, product-release specifications and/or storage conditions. The resulting PSD signature can be viewed as a function of some or all of these factors that can affect the final product. Current methods of assessing product quality are highly variable, and it is a main objective of this disclosure to exploit the merits of using appropriate particle size analysis methods and instrumentation to characterize the resulting PSD signature. Then, in an ongoing process, changes in the PSD signature arising from modifications in the formulation and/or the manufacturing process that are motivated by increased product efficacy and safety during its intended use, can be continuously monitored. The PSD signature, in effect, can become a primary indicator for product release decisions and optimum performance, as well as being useful for uncovering otherwise unrecognized defects in the manufacturing process, which may affect shelf life, performance, or both. Thus, the PSD boundaries can be defined that separate a successful liquid-based formulation from a defective one, and the optimized PSD signature can be identified that can serve as a tailored specification for achieving the desired outcome. Ultimately, this PSD signature becomes a baseline "data point" to be applied to subsequent product batches, and to which further enhancements may be made in order ultimately to improve manufacturing efficiency, as well as product quality and performance.

Exemplary aspects include: a method employing particle size analysis of particle/globule-based liquids to identify the optimum PSD signature; the particle size analysis can be capable of reproducibly yielding a measurable and relevant PSD signature; the particle size analysis technique can be selected for a given product based on particle sizes between 0.001 to 100 micrometers; ensuring the selected size range reveals defined boundaries of the optimum PSD signature; establishing a "tolerable limits threshold" that defines the pass/fail condition for particle/globule-based liquids; the shape of the PSD signature being only important with respect to the performance of the final product.

According to an exemplary aspect, the optimum PSD signature can be identifiable with the stability of particle/globule-based liquids, the compatibility of particle/globule-based liquids, the effective application of particle/globule-based liquids, the safety of particle/globule-based liquids, the manufacturing efficiency of particle/globule-based liquids, the ideal chemical form (e.g., salt, acid, base) of the active ingredient(s) in particle/globule-based liquids, the ideal chemical excipients (e.g., antioxidants, preservatives, buffers, solvents) in particle/globule-based liquids; all ingredients present of particle/globule-based liquids, all manufacturing processes of particle/globule-based liquids, all manufacturing equipment of particle/globule-based liquids, the packaging of particle/globule-based liquids, the storage of particle/globule-based liquids, the transportation of particle/globule-based liquids, stress-testing of particle/globule-based liquids, applications-testing of particle/globule-based liquids.

According to an exemplary aspect, the result can be capable of, for example, correcting product defects, deficiencies in manufacturing processes, malfunctions in manufacturing equipment, defective packaging, adverse storage conditions, and/or adverse transport processes; the result being improvements in shelf life, reductions in product waste, improvements in product application, improvements in product performance, improvements in product safety, improvements to injectable solutions, improvements to injectable emulsions, improvements to injectable liposomal dispersions, improvements to injectable micelle dispersions, improvements to commercial paints, improvements to commercial inks, improvements to commercial coatings, improvements to commercial slurries, improvements to commercial juice drinks, improvements to commercial dairy products, improvements to beverage concentrates, improvements to commercial wines, improvements to commercial asphalt emulsions.

The invention claimed is:

1. A method for identifying an improved particle size distribution profile of a dispersion, the method comprising:
   (a) providing a dispersion comprising a liquid and particles dispersed in the liquid, wherein the dispersion is a lipid emulsion, a liposomal preparation, a micellar suspension, or a colloidal or biologic/protein-based dispersion, and wherein the dispersion is suitable for intravenous administration;
   (b) measuring a particle size distribution of the dispersion, resulting in a first particle size distribution profile;
   (c) adjusting at least one parameter associated with the dispersion;
   (d) measuring a dispersion characteristic, after adjustment of the at least one parameter; and
   (e) measuring the particle size distribution of the dispersion after adjustment of the at least one parameter, resulting in a second particle size distribution profile;
   wherein each of the first and second particle size distribution profiles comprises a plurality of data points of particle concentration values as a function of particle size,
   wherein the dispersion characteristic is selected from the group consisting of: a degree of particle agglomeration at a predetermined time after dispersion formation, and a dispersion stability.

2. The method according to claim 1, wherein the dispersion contains particles in an amount of about 0.001% to about 40% w/v.

3. The method according to claim 1, wherein each particle size distribution profile consists of data points of particles having a particle size in the range of about 0.01 to about 100 micrometers.

4. The method according to claim 1, wherein the particle size distribution profiles are measured with a single-particle optical sensing technique.

5. The method according to claim 1, wherein the first particle size distribution profile and the second particle size distribution profile comprise substantially the same data points.

6. The method according to claim 1, wherein the first and second particle size distribution profiles each comprise at least 10 data points within the range of 0.01 to 100 micrometers.

7. The method according to claim 1, further comprising determining whether a change in the dispersion characteristic is attributed to a feature of the second particle size distribution profile, to define a tolerable limits threshold.

8. The method according to claim 1, wherein the dispersion characteristic is a dispersion stability.

9. The method according to claim 1, wherein the dispersion characteristic is a degree of particle agglomeration at a predetermined time after dispersion formation.

10. The method according to claim 9, further comprising determining a concentration of particle agglomerations having a particle size of at least about 5 times the size of the average particle size of unaggregated primary particles, in the dispersion.

11. The method according to claim 1, wherein the parameter associated with the dispersion is selected from the group consisting of: a material used to form the dispersion, a condition of a process for forming the dispersion, a material used to contain the dispersion, and a condition of storing and/or transporting the dispersion.

12. The method according to claim 1, wherein the step (d) of measuring a dispersion characteristic comprises subjecting the dispersion to forced accelerated degradation conditions.

13. The method according to claim 1, further comprising, after step (e):
   (f) adjusting at least one parameter associated with the dispersion;
   (g) after step (f), measuring the dispersion characteristic; and
   (h) measuring the particle size distribution of the dispersion after adjustment of the at least one parameter, resulting in a third particle size distribution profile.

14. The method according to claim 13, wherein steps (f), (g) and (h) are repeated until a predetermined condition of the dispersion characteristic is satisfied.

15. The method according to claim 14, wherein the predetermined condition is a predetermined concentration level of agglomerated particles of at least a predetermined particle size.

16. A method for improving a sample-to-sample consistency of a process for forming a dispersion, the method comprising the method of claim 1, wherein each of steps (b), (d) and (e) are conducted for at least two samples of the dispersion, wherein the at least two samples are formed in different batches in a batch process, or at different times in a continuous or semi-continuous process.

17. The method according to claim 16, wherein the particle size distribution profiles are measured with a single-particle optical sensing technique.

18. The method according to claim 16, wherein the first and second particle size distribution profiles each comprise at least 10 data points within the range of 0.01 to 100 micrometers.

19. The method according to claim 16, further comprising determining a concentration of particle agglomerations having a particle size of at least about 5 times the size of the average particle size of unaggregated primary particles, in the dispersion.

20. The method according to claim 1, wherein the particles dispersed in the liquid are solid phase particles.

21. The method according to claim 1, wherein the particles dispersed in the liquid are liquid phase particles.

22. The method according to claim 1, wherein the particles of the dispersion contain a drug.

23. The method according to claim 1, wherein the dispersion is a lipid emulsion, a liposomal preparation, or a micellar suspension.

24. A method for identifying an improved particle size distribution profile of a dispersion, the method comprising:
(a) providing a dispersion comprising a liquid and particles dispersed in the liquid, wherein the dispersion is a lipid emulsion, a liposomal preparation, a micellar suspension, or a colloidal or biologic/protein-based dispersion, and wherein the dispersion is suitable for intravenous administration;
(b) measuring a particle size distribution of the dispersion, resulting in a first particle size distribution profile;
(c) adjusting at least one parameter associated with the dispersion;
(d) measuring a dispersion characteristic, after adjustment of the at least one parameter; and
(e) measuring the particle size distribution of the dispersion after adjustment of the at least one parameter, resulting in a second particle size distribution profile;
wherein each of the first and second particle size distribution profiles comprises a plurality of data points of particle concentration values as a function of particle size,
wherein the at least one parameter adjusted in step (c) is not the same as the dispersion characteristic measured in step (d),
wherein the dispersion characteristic is selected from the group consisting of: a degree of particle agglomeration at a predetermined time after dispersion formation, and a dispersion stability.

25. The method according to claim 24, wherein the parameter associated with the dispersion is selected from the group consisting of: a material used to form the dispersion, a condition of a process for forming the dispersion, and a condition of storing and/or transporting the dispersion.

26. The method according to claim 24, wherein the particles dispersed in the liquid are solid phase particles.

27. The method according to claim 24, wherein the particles dispersed in the liquid are liquid phase particles.

28. A method for identifying an improved particle size distribution profile of a dispersion, the method comprising:
(a) providing a dispersion comprising a liquid and particles dispersed in the liquid, wherein the particles are liquid droplets, wherein the dispersion is a lipid emulsion, a liposomal preparation, a micellar suspension, or a colloidal or biologic/protein-based dispersion, and wherein the dispersion is suitable for intravenous administration;
(b) measuring a particle size distribution of the dispersion, resulting in a first particle size distribution profile;
(c) adjusting at least one parameter associated with the dispersion;
(d) measuring a dispersion characteristic, after adjustment of the at least one parameter; and
(e) measuring the particle size distribution of the dispersion after adjustment of the at least one parameter, resulting in a second particle size distribution profile;
wherein each of the first and second particle size distribution profiles comprises a plurality of data points of particle concentration values as a function of particle size.

* * * * *